Figure 1:
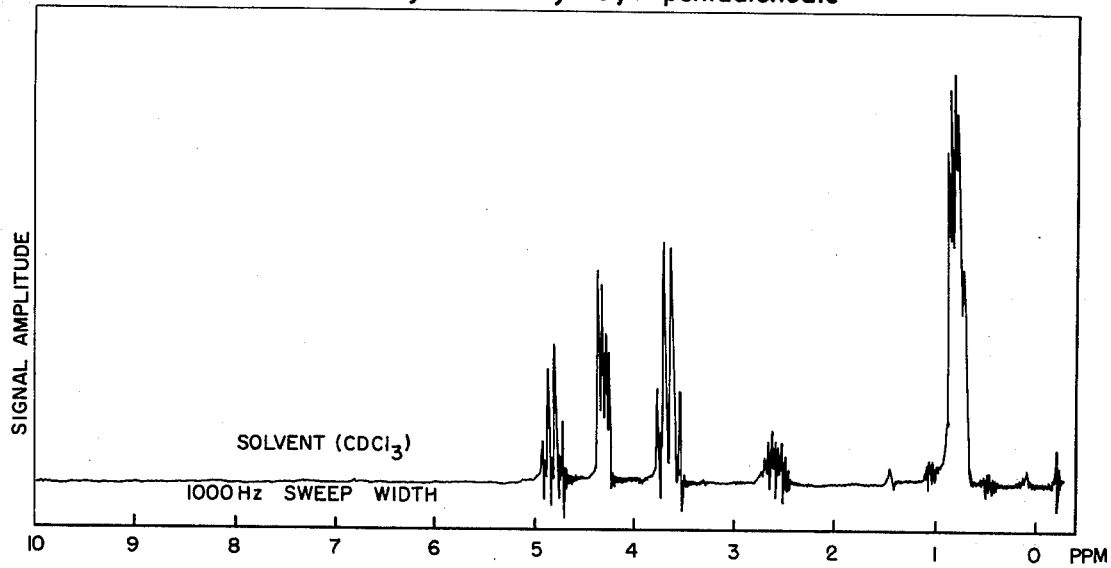

United States Patent [19]

Tseng et al.

[11] 4,000,327
[45] Dec. 28, 1976

[54] FLAVORING WITH CIS ESTERS OF 2-METHYL-3-PENTENOIC ACID

[75] Inventors: Ching Y. Tseng, Middletown; John B. Hall, Rumson; Manfred Hugo Vock, Locust; Joaquin Vinals, Red Bank, all of N.J.; Edward J. Shuster, Brooklyn, N.Y.

[73] Assignee: International Flavors & Fragrances Inc., New York, N.Y.

[22] Filed: May 9, 1975

[21] Appl. No.: 576,240

Related U.S. Application Data

[63] Continuation-in-part of Ser. No. 490,719, July 22, 1974, Pat. No. 3,931,293.

[52] U.S. Cl. .............................. 426/534; 131/17 R; 252/522
[51] Int. Cl.² ........................................ A23L 1/235
[58] Field of Search ................. 426/534; 260/486 R

[56] References Cited

UNITED STATES PATENTS

| | | | |
|---|---|---|---|
| 3,499,769 | 3/1970 | Kratz et al. | 426/534 |
| 3,931,293 | 1/1976 | Tseng et al. | 260/486 R |

OTHER PUBLICATIONS

Bedoukian, Progress in Perfumery Material, Cosmetics and Perfumery, vol. 88, No. 4, Apr. 1973, p. 31.
Mussinan et al., Organic Acids from Fresh California Strawberries, J. Agric. Food Chem., vol. 23, No. 3, 1975, pp. 482–484.
Arctander, Perfume and Flavor Chemicals, vol. 1, 1969, Publ. by the Author, Montclair, N.J., Item 1304.

*Primary Examiner*—Joseph M. Golian
*Attorney, Agent, or Firm*—Arthur L. Liberman; Harold Haidt

[57] ABSTRACT

Described is the use in berry fruit flavors of a synthetically-produced 6-carbon carboxylic acid ester-containing composition comprising as its major constituent a cis ester of 2-methyl-3-pentenoic acid having the structure:

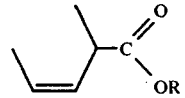

wherein R is one of ethyl, isobutyl or n-hexyl.

8 Claims, 12 Drawing Figures

EXAMPLE XXXIX
FRACTION 10

NMR SPECTRUM for Ethyl-2-methyl-3,4-pentadienoate

EXAMPLE XXXIX
FRACTION 10

INFRA RED SPECTRUM for Ethyl-2-methyl-3,4-pentadienoate

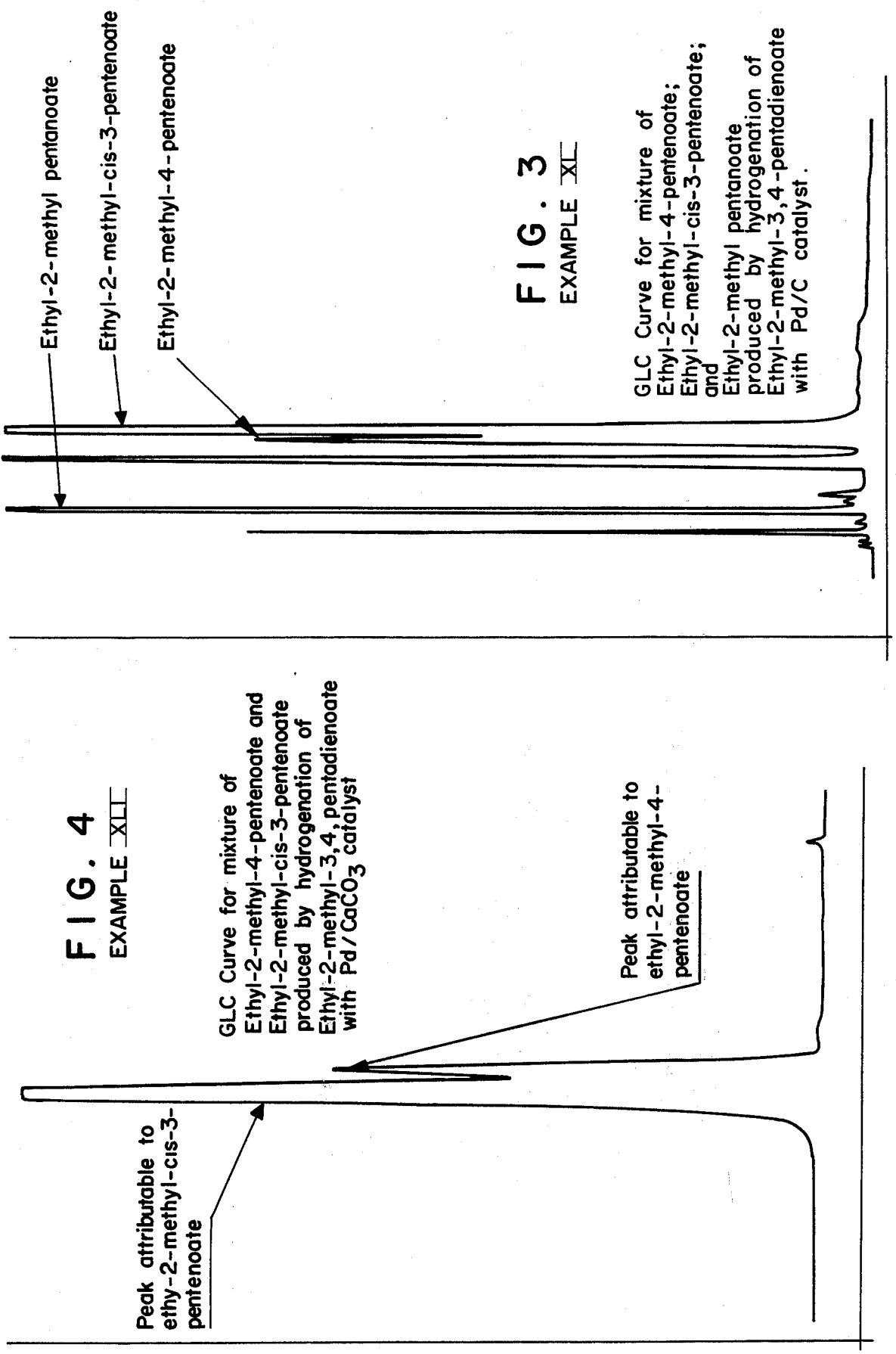

EXAMPLE XLII

EXAMPLE XLIV

NMR SPECTRUM for Hexyl-2-methyl-3,4-pentadienoate

EXAMPLE XLIV

INFRA RED SPECTRUM for Hexyl-2-methyl-3,4-pentadienoate

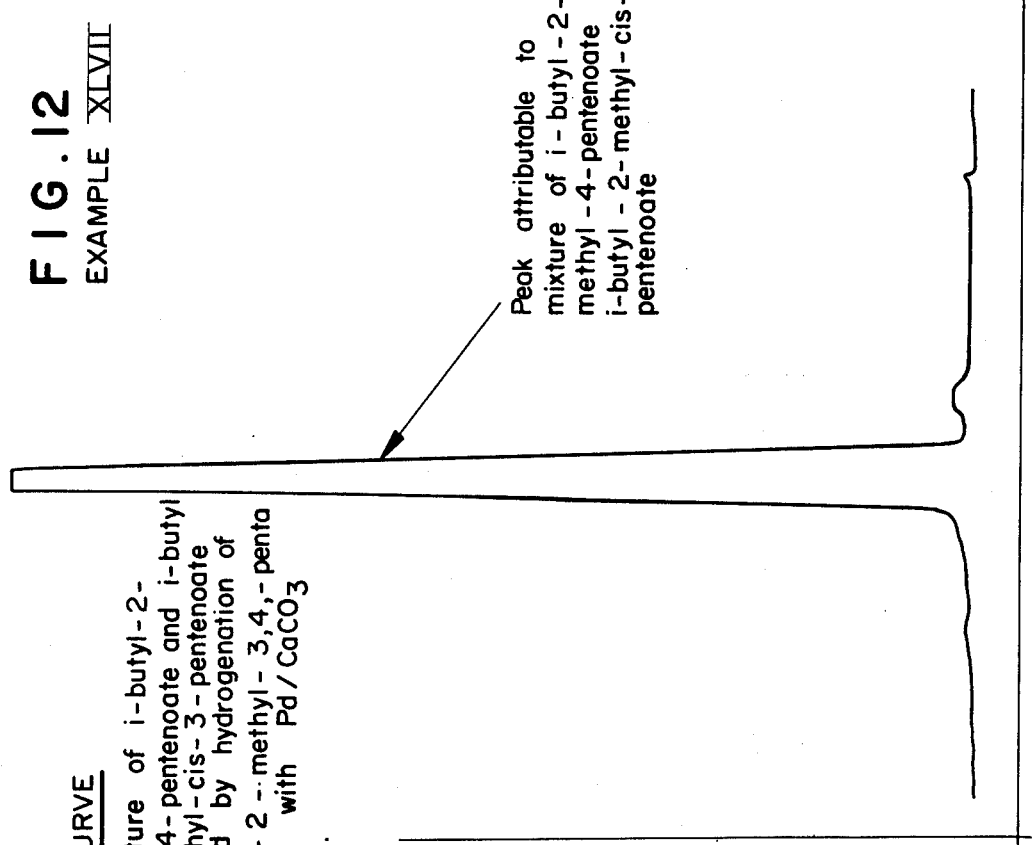

FIG. 12
EXAMPLE XLVII

Peak attributable to mixture of i-butyl-2-methyl-4-pentenoate and i-butyl-2-methyl-cis-3-pentenoate GLC CURVE
for mixture of i-butyl-2-methyl-4-pentenoate and i-butyl-2-methyl-cis-3-pentenoate produced by hydrogenation of i-butyl-2-methyl-3,4,-pentadienoate with Pd/CaCO₃ catalyst.

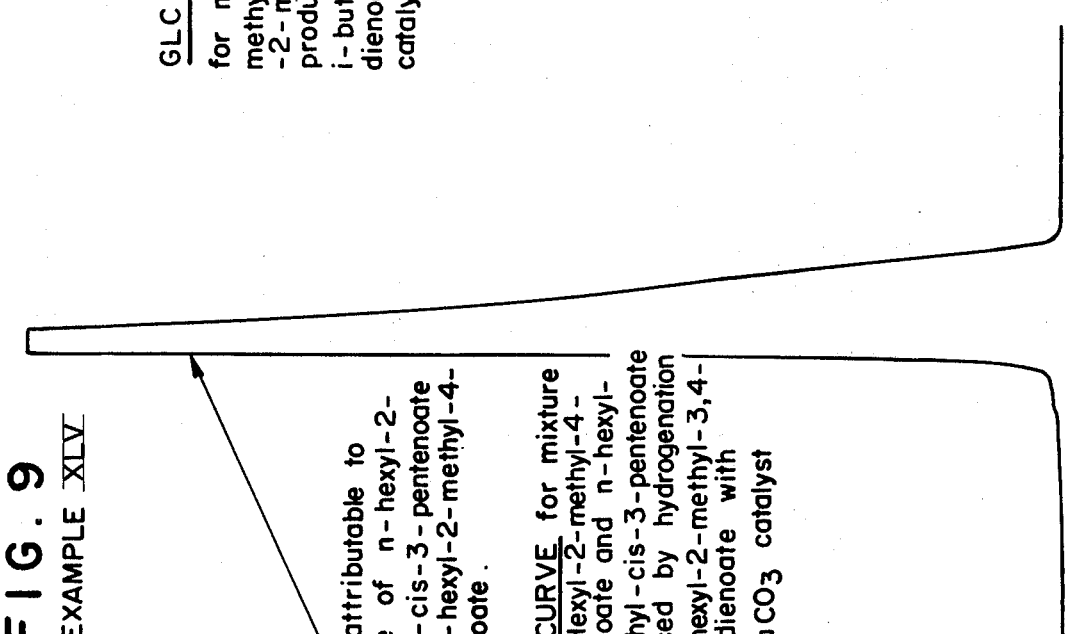

FIG. 9
EXAMPLE XLV

Peak attributable to mixture of n-hexyl-2-methyl-cis-3-pentenoate and n-hexyl-2-methyl-4-pentenoate.

GLC CURVE for mixture of n-Hexyl-2-methyl-4-pentenoate and n-hexyl-2-methyl-cis-3-pentenoate produced by hydrogenation of n-hexyl-2-methyl-3,4-pentadienoate with Pd/CaCO₃ catalyst

EXAMPLE XLVI

EXAMPLE XLVI

FLAVORING WITH CIS ESTERS OF 2-METHYL-3-PENTENOIC ACID

This application is a continuation-in-part of U.S. application Pat. Ser. No. 409,719, filed on July 22, 1974 and now U.S. Pat. No. 3,931,293, issued on Jan. 6, 1976.

BACKGROUND OF THE INVENTION

The present invention relates to 2-alkyl-cis-3-pentenoates and novel isomeric mixtures containing greater than 50% of $C_2$ –$C_6$ alkyl-2-methyl-cis-3-pentenoates produced by interalia novel processes; and to compositions using such mixtures of isomers of alkyl-2-methyl-3-pentenoates to alter the flavor and/or aroma of consumable materials.

There has been considerable work performed related to substances which can be used to impart (or enhance) flavors to (or in) various consumable materials. These substances are used to diminish the use of natural materials, some of which may be in short supply and to provide more uniform properties in the finished product. Fruity, sweet, fresh, berry, pineapple, green, herbaceous, strawberry and pear aromas, as well as fruity, berry, woody, green and pear tastes are particularly desirable for many uses in foodstuff flavors, chewing gum composition flavors and medicinal product flavors. Fruity, peppery, woody, green, herbaceous, strawberry and chamomile notes and nuances are desirable in perfume compositions. Notes having Turkish-like characteristics, as well as aromatic, sweet and bitter notes are desirable in tobacco-flavoring compositions.

U.S. Pat. No. 3,449,769 issued on March 10, 1970 discloses processes for imparting a fresh fruity flavor (particularly strawberry flavor) to foods by adding a small amount of 2-methyl-2-pentenoic acid to the foodstuff. In U.S. Pat. No. 3,449,769 it is emphasized that the basic nuance imparted by 2-methyl-2-pentenoic acid is a "berry" flavor. Quite unexpectedly, the novel "high cis" isomeric mixtures of the instant invention has properties different in kind from the 2-methyl-2-pentenoic acid of U.S. Pat. No. 3,499,769, which is only fruity and strawberry like, but does not have the sweet, pineapple, green, herbaceous and pear aroma and taste qualities of the isomeric ester mixture of the instant invention nor does it have the chamomile nuances so useful in perfumes. Isomeric ("cis" and "trans") mixtures of 2-methyl-3-pentenoic acid containing greater than 50% cis isomer are disclosed in co-pending application for U.S. Pat. No. 490,717 filed on July 22, 1974 and abandoned application No. 408,854 filed on Oct. 23, 1973 to have the following organoleptic properties:

a. In food flavorings, a sweet, fruity, strawberry, winey-cognac, butter-like, rum-like and butterscotch aroma and a sweet, strawberry, nutty-coconut, fatty, butter-like, rum-like, and butterscoth-like taste with fruity, coconut-like isovaleric undertones;

b. In perfumes, green, sweet, sharp strawberry notes; and c. In tobaccos, aromatic, sweet, bitter, slightly woody and smokey notes giving tobacco a "Turkish-like" character.

Isomeric mixture of 2-methyl-3-pentenoic acid were shown to have been prepared by Boorman and Linstead, J. Chem. Soc. 1935, 258-67 (abstracted by Chem. Abstracts, Vol. 29, pages 2912 (7/8). 2-Ethyl-3-pentenoic acid is shown to be prepared by Fichter and Obladen, Berichte, 42, 4703–7 by distillation of alpha-ethyl gamma methyl paraconic acid which, in turn, is formed by reduction using a sodium-mercury amalgam of ethyl-alpha-ethyl aceto-succinate. The above-disclosed processes produce isomer mixtures which are considered to be different in kind insofar as their organoleptic properties are concerned from the isomer mixtures produced by the processes of the instant invention.

Ethyl-2-methyl-3-pentenoate (95% 3:1 trans:cis and 5% ethyl-2-methyl-2-pentenoate) is being offered as a development chemical by Toray Industries, Inc. of 2, Nihonbashi-Muromachi 2-chome, Chuo-Ku, Tokyo, Japan. This mixture of esters is not found to be of interest as a flavor material.

McGreer, et al. Can. J. Chem., 41, 726-31 (1963) discloses the production of various alkyl esters of pentenoic and butenoic acids by means of pyrolysis of 3,5-dimethyl-3-carbomethoxy $\Delta^1$-pyrazoline. Thus, on page 728 of the McGreer article, having the following structures are shown to be produced:

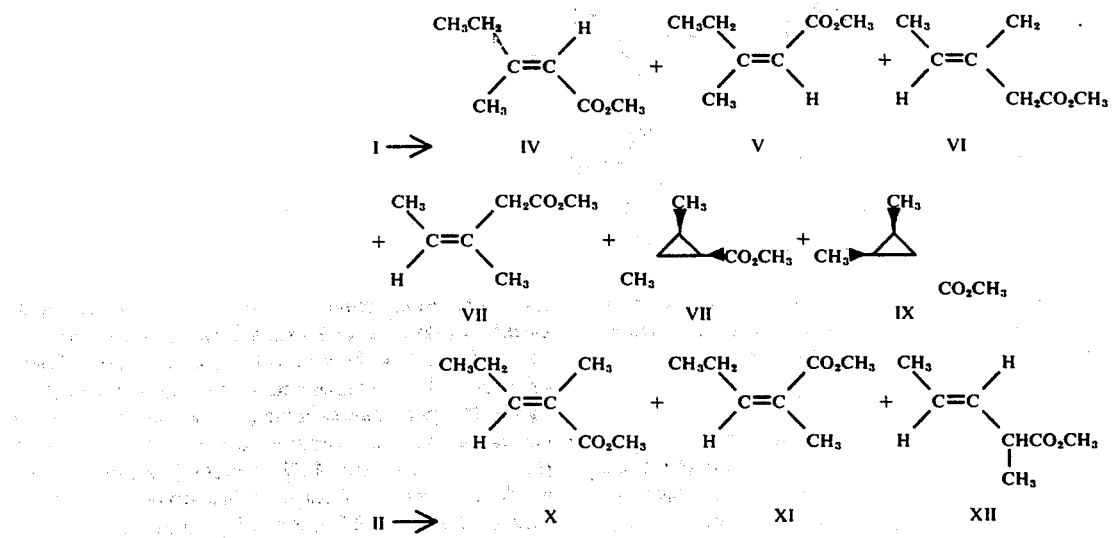

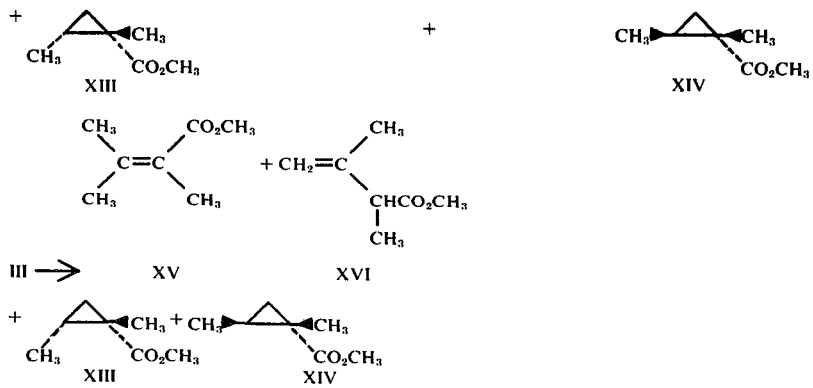

Tsuji, et al. J. Am. Chem. Soc., 86, (20) 4350–3 (1964) discloses the production of alkyl alkenoates by means of reaction of carbon monoxide, alkenyl halides and alkanols with use of palladium chloride as a catalyst. Other methods for the synthesis of alkyl alkenoates are set forth in the following references:

i. French Pat. No. 1,389,856, issued Feb. 19, 1965;
ii. Brewis and Hughes, Chem. Communications, (8), 157–8 (1965);
iii. Bordenca and Marsico, Tetrahedron Letters (16), 1541–3 (1967); and
iv. Hosaka and Tsuji, Tetrahedron, 27, (16) 3821–9 (1971).

None of the above references sets forth a process for preparing the cis isomer of an alkyl pentenoate of mixtures containing more than 50% cis isomer.

Felkin, et al. Ann. Chem. (Paris) 6 (1), 17–26 (1971) discloses processes for producing "high cis" and "high trans" methyl-2-methyl-3-pentenoate mixtures, according to the following reaction seuences:

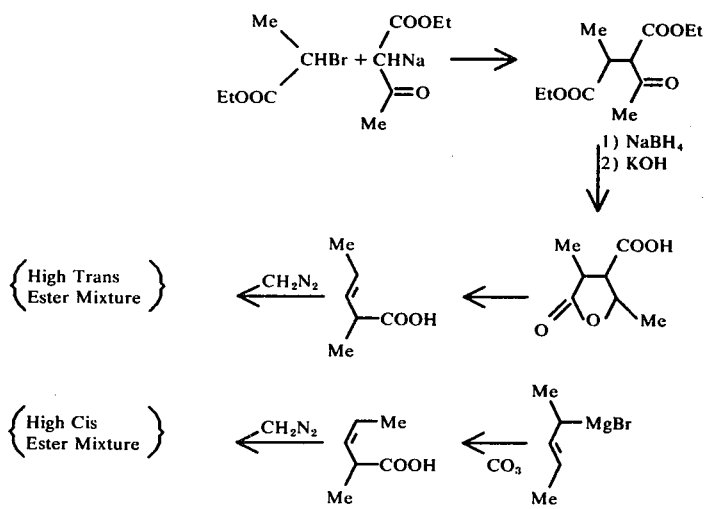

A process for preparing the "high cis" acid mixture is set forth in Felkin, et al. "Chemical" Communications, No. 802, pages 75 and 76 (Dec. 29, 1965).

THE INVENTION

It has now been discovered that novel solid and liquid foodstuff and flavoring compositions having sweet, fruity, fresh, berry, pineapple, green, herbaceous, strawberry and pear-like aromas and fruity, berry, woody, green, pear taste notes; and novel perfume compositions having fruity, peppery, woody, green, herbaceous, strawberry and chamomile notes, as well as novel tobacco flavoring compositions capable of imparting a Turkish-like character to tobacco and having aromatic, sweet, and bitter notes may be provided by the utilization of alkyl esters of 2-methyl-cis-3-pentenoic acid and isomer mixtures of alkyl-2-methyl-cis-3-pentenoates containing greater than 50% cis isomer having the generic formula:

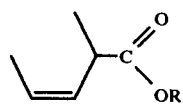

wherein R is $C_2$–$C_6$ alkyl produced either: (i) according to a process involving the steps of first preparing a 2-halo-3-pentene; then admixing said 2-halo-3-penetene with magnesium to form a 2-magnesium halo-3-penetene; then reacting said 2-magnesium halo-3-pentene with carbon dioxide to form a magnesium halo salt of 2-methyl-3-pentenoic acid; then hydrolyzing the said salt in the presence of acid to form an isomer mixture containing an approximate ratio of 60% 2-methyl-cis-3-pentenoic acid and 40% 2-methyl-trans-3-pentenoic acid; and finally, esterifying this mixture of "cis" and "trans" isomers of 2-methyl-3-pentenoic acid with an alkyl halide in basic media to form a $C_2-C_6$ alkyl-2-metyl-3-pentenoate isomer mixture; or (ii) first reacting methyl acetylene with a methyl magnesium halide to form a methylacetylene magnesium halide Grignard reagent; then reacting the metyl acetylene magnesium halide Grignard reagent with acetaldehyde to form a 3-pentyn-2-ol magnesium halide salt; then hydrolyzing the magnesium halide salt to form 3-pentyne -2-ol; then halogenating the 3-pentyne-2-ol to form a 4-halo-2-pentyne; then reacting magnesium with the 4-halo-2-pentyne to produce a 4-magnesium halo-2-pentyne Grignard reagent; then reacting the 4-magnesium halo-2-pentyne Grignard reagent with carbon dioxide to form a magnesium halo-carboxylate salt mixture of compounds having the structures:

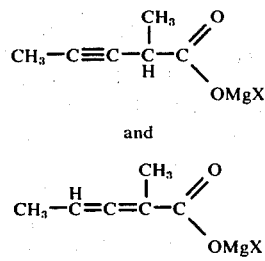

and

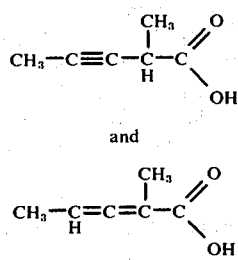

(wherein X is halogen); then hydrolyzing the magnesium halo-carboxylate salt mixture to form a mixture of carboxylic acids having the structures:

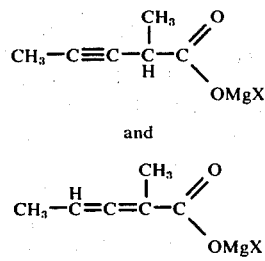

and

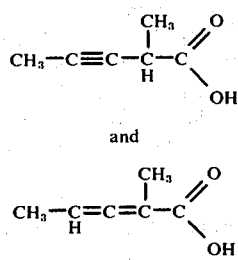

then hydrogenating the aforementioned mixture of carboxylic acids to form a mixture containing 80% 2-methyl-cis-3-pentenoic acid and 20% 2-methyl-2-pentenoic acid; then esterifying this mixture of pentenoic acids with an alkyl halide in the presence of an alkali metal hydroxide and in a solvent selected from the group consisting of hexamethyl phosphoramide, a dilower alkyl formamide and dimethyl sulfoxide; and then, optionally, separating the resulting esters to yield a substantially pure alkyl-2-methyl-cis-3-pentenoate; or (iii) first contacting with hydrogen gas one or more alkyl-2-methyl-3,4-pentadienoates having the structure:

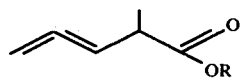

in the presence of a hydrogenation catalyst which may be either of:
 a. Raney Nickel;
 b. Palladium-on-carbon; or
 c. Palladium-on-calcium carbonate (Lindlar catalyst) at a temperature in the range of from about 10° C up to about 100° C; a hydrogen pressure in the range of from about 5 psig up to about 80 psig, the concentration of said catalyst, based on weight of the starting material, the alkyl-2-methyl-3,4-pentadienoate being from about 0.1% up to about 10%; then recovering a chemical from the reaction mass which contains at least 60% by weight of one or more alkyl-2-methyl-cis-3-pentenoates having the structure:

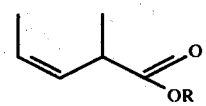

Then, optionally, separating the ingredients of the resulting chemical composition to obtain highly refined ethyl-2-methyl-cis-3-pentenoate (up to 100% alkyl-2-methyl-cis-3-pentenoate) and/or then, optionally, forming one or more carboxylic acids by means of admixing the resulting chemical composition or the hydrogenation reaction product with a basic hydrolysis agent which may be either an aqueous solution of alkali metal hydroxide, or an alcoholic solution of an alkali metal hydroxide and re-esterifying the resulting carboxylic acid by means of reacting same with an esterifying agent such as an alkanol in the presence of a protonic acid catalyst.

The term "alkyl-2-methyl-cis-3-pentenoate", as well as the structure:

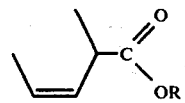

is intended herein to cover one or both stereoisomers of such material, to wit the stereoisomer having the structure:

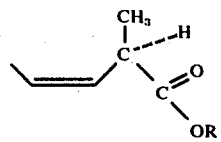

as well as the stereoisomer having the structure.

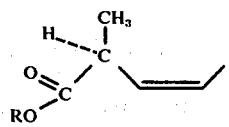

wherein R is $C_2-C_6$ lower alkyl. Further stereoisomers are possible depending upon the stereochemistry of the moiety, "R".

The 2-methyl-cis-3-pentenoic acid alkyl esters and isomer mixtures containing same of our invention are capable of supplying and/or potentiating certain flavor and aroma notes usually lacking in many fruit flavors as well as Turkish tobacco flavors heretofore provided. Furthermore, the alkyl-2-methyl-cis-3-pentenoates and isomer mixtures containing same of our invention are capable of supplying certain fragrance notes usually lacking in many perfumery materials, for example, raspberry and strawberry fragrances.

One novel process for producing one of the novel isomer mixtures of alkyl-2-methyl-3-pentenoates containing approximately a 60:40 cis-trans isomer ratio of same involves the steps of:

a. First preparing a 2-halo-3-pentene by intimately admixing either hydrogen chloride or hydrogen bromide with 1,3-pentadiene at a temperature of from −20° C up to +30° C, preferably, from 0 up to 10° C and at a pressure, preferably, of atmospheric pressure. The 1,3-pentadiene (otherwise known as "piperylene" perferably has a purity of 90% but 50% piperylene may also be used. The 2-halo-3-pentene thus produced may be used in its crude form without further purification in subsequent reactions;

b. The 2-halo-3-pentene is then reacted with magnesium to form a Grignard reagent, otherwise known as 2-magnesium halo-3-pentene. The reaction with the magnesium is carried out preferably in the presence of tetrahydrofuran, however, other solvents such as diethyl ether may also be used. The mole ratio of magnesium to halo-pentene is preferably from 1 to 10 magnesium per mole of halo-pentene, more preferably, from 3 up to 5 moles of magnesium per mole of halo-pentene. The temperature of reaction is from 10° up to 50° C; preferably from 10° up to 20° C. Temperatures lower than 10° C give rise to a reaction rate which is too slow to be economical. Temperatures higher than 50° C give rise to side reactions causing an undue lowering of the yield of product;

c. The Grignard reagent produced in step (b) is then reacted with carbon dioxide (preferably in the form of crushed dry ice). The reaction with carbon dioxide may also be carried out by bubbling carbon dioxide into the Grignard reagent at atmospheric pressure at a temperature of between −20° C up to +40° C, preferably from 0° to 20° C or reacting the Grignard reagent with gaseous carbon dioxide at higher pressures of from 10 up to 100 pounds per square inch absolute at temperatures up to 50° C. When the reaction takes place with crushed dry ice, the temperature is the temperature of crushed dry ice. The carbonation forms the magnesium halo salt of 2-methyl-3-pentenoic acid having the structure:

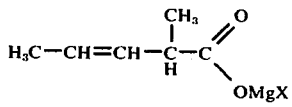

wherein X is halogen selected from the group consisting of chlorine and bromine;

d. Hydrolysis of the magnesium halo salt of 2-methyl-3-pentenoic acid in acid at a pH of from 2 up to 3. The preferred acid is a mineral acid such as hydrochloric acid or sulfuric acid;

e. Esterifying the resultant 2-methyl-3-pentenoic acid with an alkyl halide of the formula RX wherein R is $C_2$–$C_6$ alkyl and X is chloro, bromo or iodo, in the presence of an equivalent amount of base (e.g., 50% aqueous sodium hydroxide, potassium hydroxide, sodium carbonate, sodium bicarbonate or lithium hydroxide) and in the presence of a solvent, for example, hexamethyl phosphoramide, a dilower alkyl formamide, such as dimethyl formamide and dimethyl sulfoxide, at a temperature in the range of 0° C–50° C ("room temperature", 20°–30° C is preferred). The solvent ratio is in the range of from 300 g up to 900 g of solvent per mole of 2-methyl-3-pentenoic acid used with a preferred ratio of 600 g of solvent per mole of 2-methyl-3-pentenoic acid. The reaction rate is inversely proportional to the temperature of reaction; however, too high a temperature leads to isomerization of the reaction product. The reaction time can range from 2 up to 50 hours.

f. Optionally, the resulting 60:40 cis-trans alkyl-2-methyl-3-pentenoate mixture may be separated using GLC apparatus.

A second novel process for producing another of the novel isomer mixtures containing a high proportion of alkyl-2-methyl-cis-3-pentenoates, to wit approximately 80% alkyl-2-methyl-cis-3-pentenoate and 20% alkyl-2-methyl-2-pentenoate, involves the steps of:

a. First preparing a methyl acetylene magnesium halide Grignard reagent by admixing, a methyl magnesium halide (the chloride, bromide or iodide) with a slight molar excess of methyl acetylene (preferably as "Mapp Gas", commercial mixture of methyl acetylene and allene) at a temperature in the range of 40°–60° C (preferably 40°–50° C) in an inert solvent such as tetrahydrofuran or diethyl ether. Preferably, the reaction time range is from 4–12 hours;

b. Preparing 3-pentyne-2-ol by first admixing the methyl magnesium halide reaction product preferably in its original reaction solvent with a slight molar excess of acetaldehyde to form a magnesium halo salt of 3-pentyne-2-ol, at a temperature in the range of 20°–30° C and then hydrolyzing the said magnesium halo salt of 3-pentyne-2-ol, preferably with a cold concentrated mineral acid such as concentrated hydrochloric acid in ice, and purifying the resulting 3-pentyn-2-ol using standard physical separation techniques, e.g., extraction and distillation;

c. Preparing a 4-halo-2-pentyne (e.g., 4-chloro-2-pentyne or 4-bromo-2-pentyne) by means of halogenating the 3-pentyn-2-ol with a slight molar exess halogenating agent, e.g., phosphorous trichloride, phosphorous tribromide, and $SOCl_2$, at temperatures in the range of 20°–80° C, depending upon the halogenation reagent used. The preferred halogenating reagent is $PCl_3$ using a temperature range of 20°–25° C.

d. Preparing a 4-magnesium-halo-2-pentyne Grignard reagent by reaction of the 4-halo-2-pentyne with magnesium in a solvent, for example, tetrahydrofuran or diethyl ether at a temperature in the range of 25°–50° C, depending upon the solvent used;

e. Preparing a magnesium halo carboxylate salt mixture of compounds having the structures:

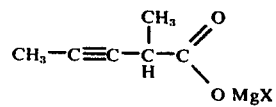

and

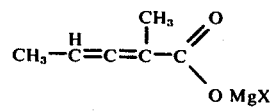

(wherein X is halogen, e.g., chloro or bromo) by intimately admixing carbondioxide (either in the gas phase, or as a solid in the form of powered dry ice). The reaction with carbondioxide may be carried out by bubbling carbon dioxide into the Grignard reagent at atmospheric pressure at a temperature of between −20° C up to +40° C, preferably, from 0° C to 20° C or reacting the Grignard reagent with gaseous carbon dioxide at higher pressures of from 10 up to 1000 pounds per square inch absolute at temperature up to 50° C. When the reaction takes place with crushed dry ice, the temperature is the temperature of crushed dry ice.

f. Hydrolyzing the resulting magnesium halo-carboxylate salt mixture with aqueous mineral acid (e.g., hydrochloric acid) at a temperature in the range of 20°–30° C to produce a crude mixture of
  i. 2-methyl-3-pentynoic acid; and
  ii. 2-methyl-2,3-pentadienoic acid
in a (i):(ii) ratio of 3:1;

g. Preparing a mixture containing about 80% 2-methyl-cis-3-pentenoic acid and 20% 2-methyl-2-pentenoic acid by hydrogenating the mixed acid product of step (f) supra in the presence of a palladium/$CaSO_4$ catalyst containing 3% Pd at a pressure in the range of 10-100 psig; preferably in the range of 20–40 psig; preferably in a lower alkanol solvent such as methanol or ethanol at temperatures in the range of 20° C –40° C, preferably 20° C –25° C. The weight percent range of catalyst is from 0.05% up to 1.5% with a range of 0.1% up to 1% being preferred. The resulting acid reaction product may be purified using standard physical separation techniques, e.g., extraction and distillation;

h. Esterifying the resultant mixture containing 80% 2-methyl-cis-3-pentenoic acid and 20% 2-methyl-2-pentenoic acid with an alkyl halide of the formula RX wherein R is $C_2$–$C_6$ alkyl and X is chloro, bromo or iodo, in the presence of an equivalent amount of base (e.g., 50% aqueous sodium, hydroxide, potassium hydroxide, sodium bicarbonate, sodium carbonate, or lithium hydroxide) and in the presence of a solvent, for example, hexamethyl phosphoramide, a dilower alkyl formamide such as dimethyl formamide and dimethyl sulfoxide, at a temperature in the range of 0° C –50° C ("room temperature", 20°–30° C is preferred). The solvent ratio is in the range of from 300 g up to 900 g of solvent per mole of 2-methyl-3-pentenoic acid used with a preferred ratio of 600 g of solvent per mole of acid reactant. The reaction rate is inversely proportional to the temperature of reaction; however, too high a temperature leads to isomerization of the reaction product. The reaction time can range from 2 up to 50 hours.

i. Optionally, the resulting ester mixture may be separated using GLC apparatus.

A third process for producing the chemical compounds useful in the practice of our invention involves the steps of:

a. First reacting a 1, 1, 1-trialkoxy propane (such as 1, 1, 1-triethoxy propane, or 1, 1, 1-trihexyloxy propane) with 2-propynol-1-in the presence of a propionic acid catalyst thereby providing the alkyl-2-methyl-3,4-pentadienoate starting material. The reaction temperature range is 120°–180° C with a range of 145°–150° C being preferred. The mole ratios of reactants preferred is 1:1 with a slight exess of either reactant being permissible. A large excess of 2-propynol-1-is undesirable, and a large excess of the trialkoxy propane is uneconomical. The percentage of propionic acid catalyst may vary from 1 up to 3%, but a 2% concentration of catalyst is preferred. Since the reaction temperature is in the range of 120°–180° C, higher pressures of reaction are required for the carrying out of the reaction, and, accordingly, pressures of from 30 up to 100 psig are used. The reaction time is inversely dependent on the temperature of reaction. Thus, for example, where the temperature range of reaction is 150°–160° C, the reaction time is approximately 3 hours. The length of reaction time varies between 2 and 6 hours, and a reaction time of 3–4 hours is preferred. The reaction product, the alkyl-2-methyl-3,4-pentadienoate, is then "worked up" and this "work up" operation is performed by first, if necessary, washing out the excess tri-alkyl orthopropionate reactant by washing with 5% hydrochloric acid solution. The acid is then neutralized by use of a sodium bicarbonate wash, and the reaction mass is then fractionally distilled.

b. The resulting alkyl-2-methyl-3,4-pentadienoate starting is then reacted with hydrogen in the presence of a Raney nickel catalyst, or a palladium-on-carbon catalyst, or a "Lindlar" catalyst (palladium-on-calcium carbonate). The percentage of palladium in the palladium-on-carbon catalyst or in the palladium-on-calcium carbonate catalyst varies from about 2% up to about 7% with a percentage of palladium in the palladium-on-carbon catalyst or in the palladium-on-calcium carbonate catalyst being preferred to be 5%. The temperature of reaction for this hydrogenation may vary from about 10° C up to about 100° C with a preferred reaction temperature of 25°–35° C. Since the reaction is exothermic, it is usually necessary to provide external cooling to the reaction mass during the course of the reaction. The pressure of hydrogen over the reaction mass may vary from about 5 psig up to about 80 psig, with the most preferred pressure being 20 psig. It has been found that pressures above 20 psig give rise to a larger amount of undesired side products. The hydrogenation reaction may be carried out in the presence of or in the absence of a solvent. When a solvent is used, it is required that it be an inert (non-reactive) solvent such as isopropyl alcohol, hexane or ethanol, with the alkyl moiety of the alcohol solvent being the same as the alkyl moiety of the alkoxy group of the ester being hydrogenated. If a solvent is used, it is preferred that the mole ratio of solvent:hydrogenated ester be approximately 1:1. Where a palladium-containing catalyst is used, the percentage of catalyst in the reaction mass may vary from 0.125% up to about 2.0% with a percentage of catalyst of about 0.25% being preferred. Where a Raney-nickel catalyst is used, the percentage of cataylst in the reaction mass may vary from about 3% up to about 10% with a percentage of catalyst of about 5% being preferred. The hydrogenation reaction produces mixtures including alkyl-2-methyl-cis-3-pentenoate, alkyl-2-methyl-4-pentenoate and alkyl-2-methyl pentanoate, all mixtures containing at least 60% alkyl-2-methyl-cis-3-pentenoate. As a result, the alkyl-2-methyl-4-pentenoate or the alkyl-2-methyl-cis-3-pentenoate may, if desired, be enriched by means of fractional distillation; or the mixtures resulting may be used as such for their organoleptic properties as perfume composition or tobacco flavoring adjuvants, or as flavor adjuvants or enhancer for use in foodstuffs, medicinal products or chewing gums. Where the catalyst used in a "Lindlar" catalyst" (palladium-on-calcium carbonate) a mixture of alkyl-2-methyl-cis-3-pentenoate and alkyl-2-methyl-4-pentenoate is produced. Where the catalyst used is palladium-on-carbon rather than palladium-on-calcium carbonate a mixture of alkyl-2-methyl-cis-3-pentenoate, alkyl-2-methyl-4-pentenoate and alkyl-2-methyl pentanoate is formed which may be used as such for its organoleptic properties as a flavor adjuvant or enhancer for foodstuffs, tobaccos, chewing gums and medicinal products or as a perfume composition or perfumed article adjuvant. Where the catalyst used is Raney nickel rather than palladium-on-calcium carbonate, initially produced is a mixture of alkyl-2-methyl-cis-3-pentenoate, alkyl-2-methyl-4-pentenoate and alkyl-2-methyl pentanoate with the percentage of alkyl-2methyl-cis-3-pentenoate being greater than 50% by weight of the total reaction product produced. As the hydrogenation proceeds, however, the percentage of alkyl-2-methyl-4-pentenoate diminishes to 0 and the percentage of alkyl-2-methyl pentanoate increases, with the quantity of alkyl-2-methyl-cis-3-pentenoate remaining about the same. In any event, at the end of the hydrogenation reaction, the reaction mass if filtered in order to separate catalyst from liquid phase desired product, and the filtrate is distilled using a fractional distillation column operated under vacuum.

c. If desired, the resulting alkyl-2-methyl-cis-3-pentenoate (and if desired other esters which may not have been separated therefrom after the hydrogenation reaction) may be converted into the corresponding carboxylic acid (for purposes of re-esterification forming other alkyl esters of 2-methyl-cis-3-pentenoic acid which are useful in the practice of our invention) by the standard saponification and acidification reactions. The saponification is preferably carried out using strong aqueous base, e.g. 50% aqueous sodium hydroxide or 50% aqueous potassium hydroxide admixed with methanol. After acidification of the resulting salt of the carboxylic acid (e.g. the sodium or potassium salt) is acidified using mineral acid (e.g. a 6 molar aqueous hydrochloric acid), and the carboxylic acid is extracted from the aqueous phase using an organic solvent such as toluene. The organic solvent is then stripped from the acid, and the acid is fractionally distilled. The resulting acid may be used as such or it may, if desired, be esterified with an alkanol to form another ester of said carboxylic acid.

The foregoing series of reactions may be illustrated as follows:

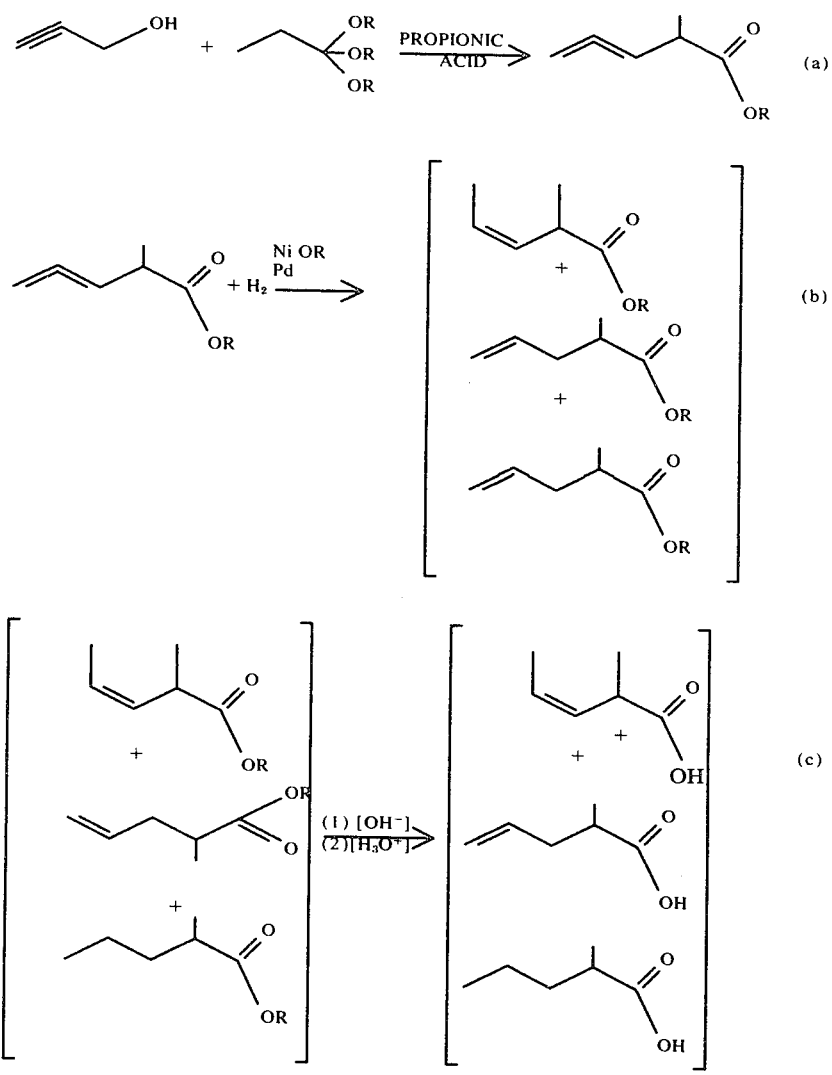

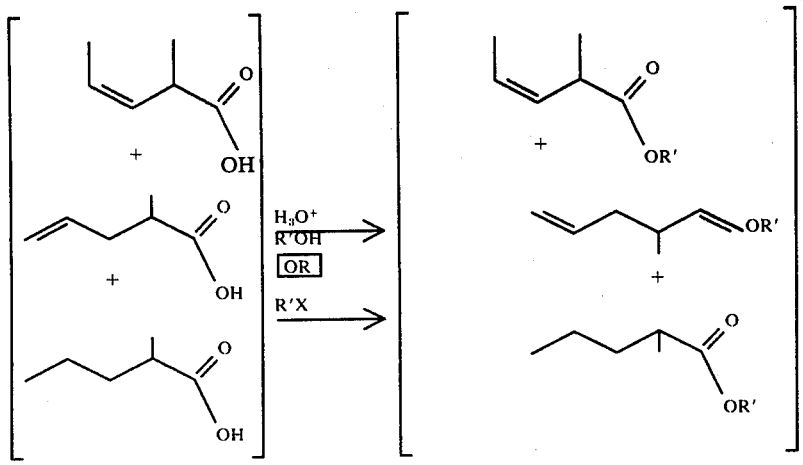

Examples of specific alkyl halide reactants, reaction products and organoleptic characteristics of such reaction products, are set forth in the following table:

| Alkyl Halide | Reaction Product | Organoleptic Properties |
|---|---|---|
| Ethyl Bromide | Ethyl-2-methyl-3-pentenoate (cis: trans ratio, approximately 3:2) | Fruity, fresh, pineapple, strawberry aroma and sweet, fruity, pineapple, strawberry, mellon-green taste at 1 ppm. Also, a fruity, green, strawberry fragrance note with a chamomile nuance. |
| Isopropyl Bromide | Isopropyl-2-methyl-3-pentenoate (cis: trans ratio, approximately 3:2) | A fruity, characteristic strawberry taste and a sweet, astringent aftertaste at 5 ppm; and a fruity, herbaceous fragrance note. |
| Isobutyl Bromide | Isobutyl-2-methyl-3-pentenoate (cis: trans ratio, approximately 3:2) | Characteristic sweet, strawberry taste, with lasting strawberry aftertaste at 5 ppm; at 10 ppm, characteristic sweeter strawberry taste with a lasting sweet strawberry after-taste. Also a fruity, woody fragrance note. |
| n-Hexyl Bromide | n-Hexyl-2-methyl-3-pentenoate (cis: trans ratio, approximately 3:2) | A pear, strawberry, fruity aroma and a sweet, strawberry pear, fruity taste at 2 ppm. In addition, fruity, peppery, chamomile and floral fragrance notes. |

When the alkyl-2-methyl-cis-3-pentenoate or isomer mixture containing more than 50% of same of our invention (hereinafter called "high cis" alkyl-2-methyl-3-pentenoate) is used as a food flavor adjuvant, or chewing gum flavor adjuvant or medicinal product flavor adjuvant, the nature of the co-ingredients included with the said "high cis" alkyl-2-methyl-3-pentenoate in formulating the product composition will also serve to alter the organoleptic characteristics of the ultimate foodstuff, chewing gum or medicinal product treated therewith.

As used herein in regard to flavors, the term "alter" in its various forms means "supplying or imparting flavor character or not to otherwise bland, relatively tasteless substances or augmenting the existing flavor characteristic where a natural flavor is deficient in some regard or supplementing the existing flavor impression to modify its quality, character or taste".

As used herein, the term "foodstuff" includes both solid and liquid ingestible materials which usually do, but need not, have nutritional value. This "foodstuffs" include soups, convenience foods, beverages, dairy products, candies, vegetables, cereals, soft drinks, snacks and the like.

As used herein, the term "medicinal product" includes both solids and liquids which are ingestible materials which have medicinal value such as cough syrups, cough drops, aspirin, and chewable medicinal tablets.

The term "chewing gum" is intended to mean a composition which comprises a substantially water-insoluble, chewable, plastic gum base such as chicle, or substitutes therefor, including jelutong, guttakay rubber or certain comestible natural or synthetic resins or waxes. Incorporated with the gum base and in admixture therewith may be plasticizers or softening agents, e.g. glycerine; and a flavoring composition which incorporates "high cis" alkyl-2-methyl-3-pentenoate or alkyl-2-methyl-cis-3-pentenoate per se of our invention, and in addition, sweetening agents which may be sugars including sucrose or dextrose and/or artificial sweeteners such as cyclamates or saccharin. Other optional ingredients may also be present.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in the selection thereof. Accordingly, such materials which may, in general, be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g., agaragar; carrageenan; cellulose and cellulose derivatives, such as carboxymethyl cellulose and methyl cellulose; natural and synthetic gums such as gum arabic, gum tragacanth; gelatin, proteinaceous materials; lipids; carbohydrates, starches, pectins and emulsufiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as caproic acid, caprylic acid, palmitic acid, myristic acid and the like, mon- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcuma and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic-acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-cis-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptanone, 4-(p-hydroxyphenyl)-2-butanone, alpha-ionone, beta-ionone, methyl-3-butanone, 2-pentanone, 2-pentenal and propanal; alcohols, such as 1-butanal, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha terpineol, cis-terpineol hydrate; esters, such as butyl acetate, ethyl acetate, ethyl acetoacetate, ethyl benzoate, ethyl butyrate, ethyl capronate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl capronate, methyl isobutyrate, alpha-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemon essential oil, bulgarian rose, yara yara, natural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, chewing gum, or medicinal product, whether simulated or natural, and should, in any event, be capable of providing an environment in which the "high cis" alkyl-2-methyl-3-pentenoate can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of "high cis" alkyl-2-methyl-3-pentenoate employed in a particular instance can vary over a relatively wide range whereby its desired organoleptic effects (having reference to the nature of the product) are achieved. Thus, correspondingly greater amounts would be necessary in those instances wherein the ultimate food composition or chewing gum or medicinal product to be flavored is relatively bland to the taste, whereas relatively minor quantities may suffice for purposes of enhancing a composition merely deficient in natural flavor or aroma. Thus, the primary requirement is that the amount selected should be "effective", i.e., sufficient to alter the organoleptic characteristics of the parent composition, whether foodstuff per se, chewing gum per se, medicinal product per se or flavoring composition. Thus, the use of insufficient quantities of "high cis" alkyl-2-methyl-3-pentenoate will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect ot ultimate food compositions, ultimate chewing gum compositions, and ultimate medicinal product compositions, it is found that quantities of "high cis" alkyl-2-methyl-3-pentenoates ranging from a small but effective amount, e.g., 0.10 parts per million up to about 50 parts per million by weight based on total composition are suitable. Concentrations in excess of the maximum quantity stated are not normally recommended since they fail to provide commensurate enhancement of organoleptic properties. In those instances wherein the "high cis" alkyl-2-methyl-3-pentenoate is added to the foodstuff or chewing gum or medicinal product as an integral component of a flavoring composition, it is of course essential that the total quantity of flavoring composition employed be sufficient to yield an effective "high cis"alkyl-2-methyl-3-pentenoate concentration in the foodstuff product, chewing gum or medicinal product.

Food flavoring compositions, chewing gum flavoring compositions and medicinal product flavoring compositions prepared in accordance with the present invention preferably contain the "high cis" alkyl-2-methyl-3- pentenoate in concentrations ranging from about 0.05% up to about 10% by weight based on the total weight of said flavoring composition.

The compositions described herein can be prepared according to conventional techniques well known, as typified by cake batters and fruit or vegetable juices, can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the "high cis" alkyl-2-methyl-3-pentenoate(s) with, for example, gum arabic, gum tragacanth, carrageenan and the like, and thereafter spray-drying the resultant mixture whereby to obtain the particular solid product. Prepared flavor mixes in powder form, e.g., a strawberry-flavored powder mix or a raspberry-flavored powder mix are obtained by mixing the dried solid components, e.g., starch, sugar and the like and the "high cis" alkyl-2-methyl-3-pentenoate in a dry blender until the requisite degree of uniformity is achieved.

It is presently preferred to combine with the "high cis" alkyl-2-methyl-3-pentenoate the following adjuvants:

Parahydroxy benzyl acetone
Vanillin
Maltol
Ethyl-3-methyl-3-phenyl glycidate
Benzyl acetate
Ethyl butyrate
Methyl cinnamate
Methyl anthranilate
Alpha-ionone
Gamma-undecalactone
Diacetyl
Anethole
Cis-3-hexenol
2-(4-hydroxy-4-methyl pentyl) norbornadiene (prepared according to Example II of application for U.S. Pat. No. 461,703 filed on Apr. 17, 1974)
Beta-ionone
Isobutyl acetate
Dimethyl sulfide
Acetic acid
Acetaldehyde
4-(2,6,6-trimethyl-1,3-cyclohexadien-1-yl)-2-butanone (prepared according to Example XVI of application for U.S. Pat. No. 386,320 filed on Aug. 7, 1973)
4-(6,6-dimethyl-2-methylene-3-cyclohexen-1-yl)-2-butanone (prepared according to Example XVI of application for U.S. Pat. No. 386,320 filed on Aug. 7, 1973)
Geraniol
Ethyl pelargonate
Isoamyl acetate
Naphthyl ethyl ether
Ethyl acetate
Isoamyl butyrate
2-Methyl-2-pentenoic acid
2-Methyl-3-pentenoic acid
Elemecine (4-allyl-1,2,6-trimethoxy benzene)
Isoelemecine (4-(1-propenyl)-1,2,6-trimethoxy benzene)

The following examples are given to illustrate embodiments of the invention as it is presently preferred to practice it. It will be understood that these examples are illustrative, and the invention is not to be considered as restricted thereto except as indicated in the appended claims. All parts and percentages set forth herein are by weight unless otherwise specified.

EXAMPLE I

PREPARATION OF AN APPROXIMATELY 60:40 CIS:TRANS MIXTURE 2-METHYL-3-PENTENOIC ACID

A. PREPARATION OF 4-CHLORO-2-PENTENE

Into a three liter flash equipped with stirrer, thermometer, reflux condenser, subsurface addition tube and inlet and outlet bubblers and cooling bath, 1000 gms (14.8 moles) of 97.7% pure piperylene is charged. The piperylene is cooled to 10° C and the reaction vessel is purged with dry nitrogen. While passing in hydrogen chloride, the reaction mass is stirred vigorously, and the reaction mass temperature is maintained at 10°–15° C with external cooling. The hydrogen chloride is added over a period of 7 hours. The reaction mass is then purged with nitrogen at room temperature for a period of 10-20 20minutes to remove any excess hydrogen chloride. The crude product may then be used further without purification for the preparation of the 2-methyl-3-pentenoic acid isomer mixture. The amount of crude product obtained is 1,435 gms.

B. PREPARATION OF 2-METHYL-3-PENTENOIC ACID ISOMER MIXTURE

Into a 12 liter reaction vessel equipped with stirrer, thermometer, reflux condenser, dropping funnel, two bubblers, heating mantle and cooling bath, thoroughly purged with nitrogen, the following materials are charged:

Magnesium Turnings—600 gms
Tetrahydrofuran—3 liters

The magnesium-tetrahydrofuran mixture is heated to 50° C at which time 70 ml of a solution (produced by admixing 750 gms of 4-chloro-2-pentene produced in step (A) with 2 liters of tetrahydrofuran) is added to the magnesiumtetrahydrofuran mixture in the 12-liter reaction vessel with stirring. The reaction mass temperature increases indicating the initiation of a Grignard reaction. With stirring, the remainder of the 4-chloro-2-pentenetetrahydrofuran solution is added over a period of 5 hours. During the first 30 minutes of the addition, the reaction mass is slowly cooled to 25°–30° C and after that time the reaction mass is maintained at 25°–30° C throughout the remainder of the addition. The reaction mass is then stirred for 1 hour at 25°–30° C.

7.2 Kilograms of finely crushed dry ice is added into a 22 liter reaction flask equipped with an air driven motor stirrer, addition tube and an inlet and outlet bubblers. The Grignard reagent produced in the 12 liter reaction vessel is siphoned onto the dry ice in the 22 liter flask thus leaving the excess magnesium turnings in the 12 liter flask. A nitrogen stream is used to prevent premature reaction of carbon dioxide at the inlet tube. The dry ice-Grignard reagent mixture is then stirred slowly until the excess carbon dioxide has evaporated. The time of stirring is 8 hours. 2.5 Liters of water is then added to dissolve the magnesium salt and tetrahydrofuran is recovered by distillation at atmospheric pressure to a pot temperature of 80° C. 1.25 Liters of toluene is then added to the reaction mass followed by 750 ml of concentrated hydrochloric acid over a period of 30 minutes maintaining the temperature of the reaction mass between 30°–40° C. The reaction mass is then stirred for another 30 minutes without further heating or cooling. The organic layer is removed and the aqueous layer is extracted with 1.25 liters of toluene after which time the two organic layers are combined. The organic solution is then stripped of solvent and the crude 2-methyl-3-pentenoic acid is rushed over to a pot temperature of 180° C at 2 mm Hg. using a 2 liter still with a 2 inch splash column. The rushed over 2-methyl-3-pentenoic acid is then fractionated at 3 mm Hg. pressure and a vapor temperature of 62°–63° C on a 1½ inch × 18 inch Goodloe packed column after adding 40 gms of Primol and 1 gm of Ionol. NMR, IR and Raman spectral analyses indicate that the material produced is a 60:40 cis:trans mixture of isomers of 2-methyl-3-pentenoic acid.

| NMR Analysis: (CDCl$_3$) | |
|---|---|
| Signal | Interpretation |
| 1.24 (d, 3H) | —CH—CH$_3$ |
| 1.69 (d, 3H) | =CH—CH$_3$ |
| (3.10) (m, 1H) (3.50) | \|<br>—CH (Shows cis-trans<br>\| ratio of 3:2) |
| 5.52 ppm (m, 2h) | —CH=CH— |

NOTE:
Signal at 3.50 ppm attributed to "cis" isomer, and 3.10 ppm attributed to "trans" isomer.

EXAMPLE II

PREPARATION OF (i) MIXTURE OF 60% CIS ETHYL-2-METHYL-3-PENTENOATE AND 40% TRANS-ETHYL-2-METHYL-3-PENTENOATE AND (ii) CIS ETHYL-2-METHYL-3-PENTENOATE

Into a 500 ml flask equipped with magnetic stirring bar, the following ingredients are added while maintaining the temperature at 20°–25° C using an ice water cooling bath and with stirring:

| (i) 2-methyl-3-pentenoic acid 60:40 cis:trans isomer mixture (produced according to Example I) | 38 g (0.33 moles) |
|---|---|
| (ii) Ethyl bromide | 40 g (0.37 moles) |
| (iii) Sodium hydroxide (50% aqueous solution) | 32 g (0.40 moles) |
| (iv) Hexamethyl phosphoramide | 200 g |

The reaction mass is stirred for a period of 15 hours at room temperature. 300 ml water is then added to the mass and the solution is extracted with 200 ml of diethyl ether. The ether extract is washed with 20 ml of 20% sodium chloride solution, and is then concentrated by means of rotary evaporation. The resulting residue (32 grams) is distilled at 50 mm Hg. pressure with a semi-micro distillation apparatus, thereby giving 23 g of ethyl-2-methyl-3-pentenoate (chemical yield: 50%). Boiling point: 75° C at 50 mm Hg. pressure. The ratio is cis isomer to trans isomer is 3:2.

| (A) NMR Spectrum of mixture of cis and trans isomer of ethyl-2-methyl-3-pentenoate ester (CDCl$_3$) | |
|---|---|
| Signal | Interpretation |
| 1.24 (d, 3H) | —CH—CH$_3$ |
| 1.25 (t, 3H) | —O—CH$_2$—CH$_3$ |
| 1.65 (d, 3H) | =CH—CH$_3$ |
| (3.05) (m, 1H) (3.45) | \| (Area integral<br>—CH indicates that<br>\| cis:trans isomer<br>ratio is 3:2) |
| 4.10 (q, 2H) | —C—O—CH$_2$—CH$_3$<br>\|\|<br>O |
| 5.50 ppm (m, 2H) | —CH=CH— |

The mixture is separated using GLC trapping.

GLC CONDITIONS

Column: 20'× ¼" OD 5% OV-25 on 80/100 mesh Chromosorb G stainless steel
Flow: 100 ml/min Helium Temperature:
Column = 150° isothermal
Injector = 230°
Detector (T.C.) = 260°
The individual NMR analyses (CDCl$_3$) are as follows:

| (B) Cis isomer of ethyl-2-methyl-3-pentenoate: NMR Analysis (CDCl$_3$): | |
|---|---|
| Signal | Interpretation |
| 1.22 (d, 3H) | —CH—CH$_3$ |
| 1.28 (t, 3H) | —CH$_2$—CH$_3$ |
| 1.66 (d, 3H) | C=CH—CH$_3$ |
| 3.44 (m, 1H) | \|<br>—CH<br>\| |
| 4.15 (q, 2H) | O<sub>≳</sub>C—O—CH$_2$—CH$_3$ |
| 5.52 ppm (m, 2H) | —CH=CH— |

| (C) Trans isomer of ethyl-2-methyl-3-pentenoate: NMR Analysis (CDCl$_3$) | |
|---|---|
| signal | Interpretation |
| 1.22 (d, 3H) | —CH—CH$_3$ |
| 1.28 (t, 3H) | —CH$_2$—CH$_3$ |
| 1.66 (d, 3H) | C=CH—CH$_3$ |
| 3.10 (m, 1H) | \|<br>—CH<br>\| |
| 4.15 (q, 2H) | O<sub>≳</sub>C—O—CH$_2$—CH$_3$ |
| 5.52 ppm (m, 2H) | —CH=CH— |

EXAMPLE III

PREPARATION OF THE ESTERS: (i) ISOPROPYL-2-METHYL-3-PENTENOATE: AND (ii) ISOBUTYL-2-METHYL-PENTENOATE

Into a 250 ml flask equipped with magnetic stirring bar and operated at 20°–25° C, using external cooling, the following materials are added:

| | | |
|---|---|---|
| (i) | 2-methyl-3-pentenoic acid produced according to the process of Example I | 17.1 g (0.15 moles) |
| (ii) | Iodomethane | 4.26 g (0.03 moles) |
| (iii) | Isopropyl bromide | 3.6 g (0.03 moles) |
| (iv) | Isobutyl bromide | 4.11 g (0.03 moles) |
| (v) | Isoamyl bromide | 4.53 g (0.03 moles) |
| (vi) | Sodium hydroxide (50% aqueous solution) | 16.0 g (0.2 moles) |
| (vii) | Hexamethyl phosphoramide | 180 g |

The reaction mass is stirred for a period of 72 hours while maintaining the reaction mass temperature at 20°–25° C. At the end of the 72 hour period, the reaction mass is diluted with 100 ml of water and extracted with two 100 ml portions of diethyl ether. The diethyl ether extract is then evaporated, leaving a residue. The residue is rush-distilled at 0.3 mm Hg. pressure yielding 6 g of an oil. GLC analysis indicates at least two major and three minor components. The major components are trapped and certified by mass spectral and NMR analysis to be iospropyl-2-methyl-3-pentenoate and isobutyl-2-methyl-3-pentenoate. The GLC conditions are as follows: 100°–200° C; 6° C/minute; ¼ inch × 10 feet — 5% carbowax packed column.

NMR Analysis (CDCl$_3$) for isopropyl-2-methyl-3-pentenoate (having a cis:trans mole ratio of 3:2):

| Signal | Interpretation |
|---|---|
| 1.22 (d, 9H) | —CH—CH$_3$ |
| 1.70 (d, 3H) | =CH—CH$_3$ |
| (3.0) (m, 1H) (3.40) | —CH— (Area integral indicates that cis:trans isomer ratio is 3:2) |
| 5.0 (m, 1H) | >C(=O)—O—CH< |
| 5.52 ppm (m, 2H) | —CH=CH— |

NMR Analysis (CDCl$_3$) for isobutyl-2-methyl-3-pentenoate (having a cis-trans mole ratio of 3:2):

| Signal | Interpretation |
|---|---|
| 0.97 (d, 6H) | —CH—CH$_3$ |
| 1.04 (d, 3H) | —C(=O)—CH—CH$_3$ |
| 1.70 (d, 3H) | =CH—CH$_3$ |
| 1.90 (m, 1H) | —C—CH— |
| (3.10) (m, 1H) (3.50) | —C(=O)—CH— (Shows that cis:trans isomer ratio is 3:2) |
| 3.88 (d, 2H) | >C(=O)—O—CH$_2$— |
| 5.52 ppm (m, 2H) | —CH=CH— |

EXAMPLE IV

PREPARATION OF n-HEXYL-2-METHYL-3-PENTENOATE 3:2 CIS:TRANS ISOMER MIXTURE

Into a 125 ml reaction vessel equipped with magnetic stirrer and maintained at room temperature, the following materials are added:

| | | |
|---|---|---|
| (i) | 2-methyl-3-pentenoic acid isomer mixture prepared according to Example I | 1.1 g (0.01 moles) |
| (ii) | 1-bromo hexane | 2.0 g (0.012 moles) |
| (iii) | Hexamethyl phosphoramide | 20 g |
| (iv) | Sodium hydroxide (50% aqueous solution) | 1.0 g (0.012 moles) |

The reaction mass is stirred for a period of three hours at room temperature. It is then diluted with 100 ml of water and extracted with 50 ml of diethyl ether. The resulting ether extract is washed with three 10 ml portions of 20% aqueous sodium chloride solution. The ether is then evaporated to yield 2.0 g of an oil. GLC analysis indicates 67% n-hexyl-2-methyl-3-pentenoate. The mixture of esters is separated by GLC trapping.

NMR Analysis (CDCl$_3$) indicating that it is a mixture of cis and trans isomers with the ratio of cis isomer: trans isomer being 3:2 and is as follows:

| Signal | Interpretation |
|---|---|
| 0.90 (t, 3H) | CH$_3$—CH$_2$— |
| 1.24 (d, 3H) | CH$_3$—CH— |
| 1,28 (m, 6H) | —CH$_2$— |
| 1.64 (m, 5H) | —CH$_2$—C—O and =C—CH$_3$ |
| (3.10) (m, 1H) (3.44) | —CH— (Area integral indicates that cis:trans isomer ratio is 3:2) |
| 4.08 (t, 2H) | —CH$_2$—O—C(=O) |
| 5.52 ppm (m, 2H) | —CH=CH— |

EXAMPLE V

FLAVOR FORMULATION CONTAINING ETHYL-2-METHYL-3-PENTENOATE 3:2 CIS:TRANS ISOMER MIXTURE

The following basic strawberry formulation is prepared:

| Ingredient | Parts by Weight |
|---|---|
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |

-continued

| Ingredient | Parts by Weight |
|---|---|
| Alpha-ionone | 0.1 |
| Gamma undecalactone | 0.2 |
| Diacetyl | 0.2 |
| Anethole | 0.1 |
| Cis-3-hexenol | 1.7 |
| 95% Aqueous ethanol | 38.5 |
| Propylene glycol | 50.0 |
| | 100.0 |

To a portion of the foregoing formulation, 0.2% by weight of ethyl-2-methyl-3-pentenoate, 3:2 cis:trans isomer mixture prepared according to the process of Example II is added. The formulation with the ethyl-2-methyl-3-pentenoate is compared to the same formulation without said ethyl-2-methyl-3-pentenoate.

Both flavors are evaluated in a milk beverage sweetened with 10% sugar at the rate of 100 ppm. Both beverages are tasted by an expert panel. The beverage containing the strawberry formulation with the addition of ethyl-2-methyl-3-pentenoate is unanimously preferred as having a more natural like, delicate strawberry aroma, a sweeter, more pleasant, strawberry taste and a sweet, strawberry after-taste.

EXAMPLE VI

RASPBERRY PERFUME FORMULATION

The following formulation is prepared:

| Ingredient | Parts by Weight |
|---|---|
| Ethyl-2-methyl-3-pentenoate 3:2 cis:trans isomer mixture prepared according to the process of Example II | 10 |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl acetate | 50 |
| 4-(parahydroxyphenyl)-2-butanone | 50 |
| Ethyl laurate | 30 |
| Ethyl isovalerate | 10 |
| Ethyl butyrate | 50 |
| Cinnamyl cinnamate | 20 |
| | 419 |

The ethyl-2-methyl-3-pentenoate imparts to this raspberry perfume formulation a delicate raspberry topnote nuance.

EXAMPLE VII

TOBACCO FLAVOR FORMULATION AND TOBACCO

A tobacco mixture is produced by admixing the following materials:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.

The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the ethyl-2-methyl-3-pentenoate 3:2 cis:trans isomer mixture produced according to the process of Example II. The control cigarettes not containing the ethyl-2-methyl-3-pentenoate isomer mixture produced according to the process of Example II and the experimental cigarettes which do contain the ethyl-2-methyl-3-pentenoate isomer mixture produced according to the process of Example II are evaluated by paired comparison, and the results are as follows:

In aroma, the cigarettes containing the ethyl-2-methyl-3-pentenoate isomer mixture have been found to be more aromatic.

In smoke flavor, the cigarettes containing the ethyl-2-methyl-3-pentenoate isomer mixture are more aromatic, more sweet, more bitter, slightly less harsh in the mouth and throat and leave a slight, sweet chemical mouth-coating effect similar to Turkish tobacco.

In summary, the ethyl-2-methyl-3-pentenoate isomer mixture enhances the tobacco-like taste and aroma of a blended cigarette and imparts to that cigarette a Turkish-like character is smoke flavor.

EXAMPLE VIII

The following concentrate is prepared:

| Ingredient | Percent |
|---|---|
| Geraniol | 1.00 |
| Ethyl methyl phenyl glycidate | 3.33 |
| Isopropyl-2-methyl-3-pentenoate 3:2 cis:trans isomer mixture prepared according to the process of Example III | 4.77 |
| Vanillin | 5.66 |
| Ethyl pelargonate | 13.06 |
| Isoamyl acetate | 14.00 |
| Ethyl butyrate | 58.18 |

EXAMPLE IX

| Ingredient | Percent |
|---|---|
| Naphthyl ethyl ether | 0.96 |
| Vanillin | 2.66 |
| Ethyl methyl phenyl glycidate | 2.88 |
| Isobutyl-2-methyl-3-pentenoate 3:2 cis:trans isomer mixture prepared according to the process of Example III | 4.90 |
| Ethyl acetate | 9.58 |
| Isoamyl acetate | 12.25 |
| Ethyl butyrate | 26.20 |
| Isoamyl butyrate | 40.57 |

EXAMPLE X

100 Parts of the concentrate prepared in Example VIII is dissolved in 400 parts of propylene glycol and the mixture is added to a hard candy melt at the rate of 1.5 oz of the concentrate solution per 100 lbs. of melt. After the finished candy has been produced, it is found to have an excellent strawberry flavor. When the candy is compared with candy made under the same conditions, but without the isopropyl-2-methyl-3-pentenoate prepared according to the process of Example III in the concentrate, it is found to have an inferior strawberry flavor.

EXAMPLE XI

A propylene glycol solution of the concentrate (1 part concentrate:4 parts of propylene glycol) as prepared in Example IX is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing 1 oz. of the flavored, acidified syrup with 5 oz. of carbonated water. The beverage so prepared has an excellent fresh strawberry flavor, and is found to be markedly superior to a beverage prepared in the same manner but without the isobutyl-2-methyl-3-pentenoic isomer mixture prepared according to the process of Example III.

EXAMPLE XII

The flavor concentrate prepared in Example IX is admixed with gum arabic in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the isobutyl-2-methyl-3-pentenoate isomer mixture prepared according to the process of Example III in the concentrate.

EXAMPLE XIII

The following mixture is prepared:

| Ingredient | Parts by Weight |
|---|---|
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |
| Ethyl Heptanoate | 1 |
| Dulcinyl | 5 |
| 2(para-hydroxyphenyl)-3-butanone | 2 |
| Ethyl acetate | 1 |
| Beta-ionone | 10 |
| Palatone | 2 |
| Ethyl vanillin | 1 |
| Ethyl-3-methyl-3-phenyl glycidate | 150 |
| n-hexyl-2-methyl-3-pentenoate 3:2 cis:trans isomer mixture prepared according to the process of Example IV | 5 |

The n-Hexyl-2-methyl-3-pentenoate isomer mixture prepared according to the process of Example IV imparts a fruity, chamomile, peppery, floral note to this strawberry fragrance.

EXAMPLE XIV

PREPARATION OF SOAP COMPOSITION

One hundred grams of soap chips are mixed with one gram of the perfume composition of Example VI until a substantially homogeneous composition is obtained. The perfumed soap composition manifests an excellent raspberry character with a delicate raspberry topnote nuance.

EXAMPLE XV

PREPARATION OF A DETERGENT COMPOSITION

A total of 100 g of a detergent powder is mixed with 0.15 g. of the perfume composition of Example VI until a substantially homogeneous composition is obtained. This composition has an excellent raspberry fragrance.

EXAMPLE XVI

PREPARATION OF A COSMETIC POWDER COMPOSITION

A cosmetic powder is prepared by mixing in a ball mill 100 g of talcum powder with 0.25 g of n-hexyl-2-methyl-3-pentenoate 3:2 cis:trans isomer mixture prepared according to Example IV. Is has an excellent fruity, chamomile aroma.

EXAMPLE XVII

PERFUMED LIQUID DETERGENT

Concentrated liquid detergents with a fruity, chamomile odor are prepared containing 0.10%, 0.15% and 0.20% of n-hexyl-2-methyl-3-pentenoate prepared according to the process of Example IV. They are prepared by adding and homogeneously mixing the appropriate quantity of n-hexyl-2-methyl-3-pentenoate prepared according to the process of Example IV in the liquid detergent. The detergents all possess a fruity, chamomile fragrance, the intensity increasing with greater concentration of n-hexyl-2-methyl-3-pentenoate isomer mixture prepared according to the process of Example IV.

EXAMPLE XVIII

PREPARATION OF A COLOGNE AND HANDKERCHIEF PERFUME

Isopropyl-2-methyl-3-pentenoate 3:2 cis:trans isomer mixture prepared according to the process of Example III is incorporated in a cologne at a concentration of 2.5% in 85% aqueous ethanol; and into a handkerchief perfume at a concentration of 20% (in 95% aqueous ethanol). A distinct and definite strong fruity, herbaceous fragrance is imparted to the cologne and to the handkerchief perfume.

EXAMPLE XIX

PREPARATION OF A COLOGNE AND HANDKERCHIEF PERFUME

The composition of Example XIII is incorporated in a cologne at a concentration of 2.5% in 85% aqueous ethanol; and into a handkerchief perfume at a concentration of 20% (in 95% aqueous ethanol). The use of the n-hexyl-2-methyl-3-pentenoate isomer mixture in the composition of Example XIII affords a distinct and definite strong strawberry aroma with a chamomile note to the handkerchief perfume and cologne.

EXAMPLE XX

PREPARATION OF SOAP COMPOSITION

One hundred grams of soap chips are mixed with one gram of n-hexyl-2-methyl-3-pentenoate 3:2 cis:trans isomer mixture prepared according to the process of Example IV until a substantially homogeneous composition is obtained. The perfumed soap composition manifests an excellent raspberry aroma with fruity and green notes and a chamomile nuance.

EXAMPLE XXI

PREPARATION OF A DETERGENT COMPOSITION

A total of 100 g of a detergent powder is mixed with 0.15 g of the isomer mixture of 3:2 cis:trans ethyl-2-methyl-3-pentenoate of Example II until a substantially homogeneous composition is obtained. This composition has an excellent strawberry aroma with fruity and green notes and a chamomile nuance.

EXAMPLE XXII

PREPARATION OF A COSMETIC POWDER COMPOSITION

A cosmetic powder is prepared by mixing in a ball mill 100 g of talcum powder with 0.25 of ethyl-2-methyl-3-pentenoate 3:2 cis:trans isomer mixture prepared according to Example II. It has an excellent fruity, green, strawberry character with a chamomile nuance. The same cosmetic powder is then further admixed in a ball mill with 0.25 g of isopropyl-2-methyl-3-pentenoate 3:2 cis:trans isomer mixture prepared according to Example III. The cosmetic powder now has an added herbaceous note.

EXAMPLE XXIII

PERFUMED LIQUID DETERGENT

Concentrated liquid detergents with green, fruity, strawberry notes and chamomile nuances are prepared containing 0.10%, 0.15% and 0.20% of ethyl-2-methyl-3-pentenoate 3:2 cis:trans isomer mixture prepared according to Example II. They are prepared by adding and homogeneously mixing the appropriate quantity of ethyl-2-methyl-3-pentenoate isomer mixture in the liquid detergent. The detergents all possess fruity, green, strawberry notes with chamomile nuances, the intensity increasing with greater concentrations of ethyl-2-methyl-3-pentenoate isomer mixture.

EXAMPLE XXIV

PREPARATION OF A COLOGNE AND HANDKERCHIEF PERFUME

Ethyl-2-methyl-3-pentenoate 3:2 cis:trans isomer mixture prepared according to Example II is incorporated in a cologne at a concentration of 2.5% in 85% aqueous ethanol; and into a handkerchief perfume at a concentration of 20% (in 95% aqueous ethanol). A distinct, fruity, green, strawberry aroma with a chamomile nuance is imparted to the cologne and to the handkerchief perfume.

EXAMPLE XXV

PREPARATION OF MIXTURE CONTAINING 80% CIS-2-METHYL-3-PENTENOIC ACID AND 20% 2-PENTENOIC ACID

A. PREPARATION OF 3-PENTYN-2-OL

| Equipment: | 5 liter reaction flask | |
|---|---|---|
| Material: | Methyl magnesium chloride (3 molar in tetrahydrofuran) | 3 liters |
| | Mapp gas (Mixture of methyl acetylene and allene) | 600 g |
| | Acetaldehyde (6 molar) | 264 g |

Procedure: Mapp gas is passed through a sodium hydroxide dying tube into the methyl magnesium chloride solution at 40°–50° C. The operation takes 5 hours to completion. The mixture is heated at 50° C for an additional 2 hours before cooling. To the cold solution is added 264 g of acetaldehyde at 20°–30° C over 2 hours with cooling. The mixture is then stirred for 1 hour at 25° C and is then decomposed with 800 ml of concentrated hydrochloric acid and 5 kg of ice. The resulting lower layer is extracted with one liter of benzene. The combined organic liquids are washed with two 200 ml portions of 20% aqueous NaCl and distilled at atmospheric pressure to a pot temperature of 92° C and then rushed over under vacuum. The rushed over material is then topped at 45–50 mm Hg. pressure to a pot temperature of 72° C. After the topping, this material is used to prepare 4-chloro-2-pentyne in part B, infra, without further purification.

B. PREPARATION OF 4-CHLORO-2-PENTYNE

| Equipment: | 250 ml reaction flask | |
|---|---|---|
| Material: | 3-Pentyn-2-ol | 84 g (1 mole) |
| | Phosphorous trichloride | 69 g (0.5 mole) |

Procedure: The phosphorous trichloride is added at 20°–25° C with cooling to the 3-pentyn-2-ol prepared in part A, supra. The mixture is stirred for 12 hours at 20°–25° C and then heated to 72° C for 5 hours. IR analysis indicates that the reaction is complete. The material is then rushed over under vacuum to give 4-chloro-2-pentyne for the Grignard reaction exemplified in part C, infra. The yield is nearly quantitative.

C. PREPARATION OF 2-METHYL-3-PENTYNOIC ACID

| Equipment: | 1 liter reaction flask | |
|---|---|---|
| Material: | 4-chloro-2-pentyne | 46 g (0.5 mole) |
| | Magnesium chips | 60 g (2.5 mole) |
| | Tetrahydrofuran (dry) | 500 ml |

Procedure: 4-Chloro-2-pentyne is dissolved in 200 ml of tetrahydrofuran and added over 4½ hours (after starting the reaction with iodine crystals) to the magnesium chips in 300 ml of tetrahydrofuran. The reaction temperature rises to 44°–50° C in the initiation period and is maintained at 28°–30° C with external cooling. The reaction mixture is allowed to stir for an additional hour after all of the 4-chloro-2pentyne is added. The resulting Grignard reagent is poured onto 620 g of dry ice (powdered) with stirring. After the $CO_2$ evaporates, 300 ml of water is added and the solution is extracted with three 200 ml portions of toluene. The toluene extracts are discarded. The aqueous solution is cooled and acidified with 50 ml of concentrated hydrochloric acid; then extracted with two 200 ml portions of toluene. The toluene extract, after washing with three 50 ml portions of 20% NaCl solution is stripped of solvent and rushed over to give 22 g of crude acids. The crude product is then fractionated in a semi-micro still to give 6.2 g of an acid mixture which contains a 3:1 mixture of 2-methyl-3-pentynoic acid and 2-methyl-2,3-pentadienoic acid.

D. HYDROGENATION REACTION

| Equipment: | Parr Shaker | |
|---|---|---|
| Material: | Mixture of 2-methyl-3-pentynoic acid and 2-methyl-2,3-pentadienoic acid | 4 g |
| | Methanol (absolute) | 50 ml |
| | 3% Pd/CaSO₄ | 0.1 g |

Procedure: The 2-methyl-3-pentynoic acid and 2-methyl-2,3-pentadienoic acid mixture produced in part C, supra is hydrogenated at room temperature in methanol in the presence of Pd/CaSo₄ catalyst at a hydrogen pressure of approximately 40 psig. The reaction is complete in 5 minutes. After removal of the methanol, the residue oil is analyzed by GLC which shows one peak. However, NMR analysis shows two products confirmed to be cis-2-methyl-3-pentenoic acid and 2-methyl-2-pentenoic acid. (A 4:1 mixture).

EXAMPLE XXVI

PREPARATION OF MIXTURE OF 80% ETHYL-2-METHYL-CIS-3-PENTENOATE AND 20% ETHYL-2-METHYL-2-PENTENOATE

Into a 500 ml flask equipped with magnetic stirring bar, the following ingredients are added while maintaining the temperature at 20°–25° C using an ice water cooling bath and with stirring:

| (i) | Mixture of 80% cis-2-methyl-3-pentenoic acid and 20% 2-methyl-2-pentenoic acid (produced according to the process of Example XXV) | 38 g (0.33 moles) |
|---|---|---|
| (ii) | Ethyl bromide | 40 g (0.37 moles) |
| (iii) | Sodium hydroxide (50% aqueous solution) | 32 g (0.40 moles) |
| (iv) | Hexamethyl phosphoramide | 200 g |

The reaction mass is stirred for a period of 15 hours at room temperature. 300 ml water is then added to the mass and the solution is extracted with 200 ml of diethyl ether. The ether extract is washed with 20 ml of 20% sodium chloride solution, and is then concentrated by means of rotary evaporation. The resulting residue (32 grams) is distilled at 55 mm Hg. pressure with a semi-micro distillation apparatus, thereby giving 23 g of a mixture containing 80% cis-ethyl-2-methyl-3-pentenoate and 20% ethyl-2-methyl-2-pentenoate.

The mixture is separated using GLC trapping.
GLC Conditions:
Column: 20' × ¼" OD 5% OV-25 on 80/100mesh Chromosorb G stainless steel
Flow: 100 ml/min Helium
Temperature:
Column = 150° isothermal
Injector = 230°
Detector (T.C.) = 260°

The NMR analysis (CDCl₃) of the cis isomer of ethyl-2-methyl-3-pentenoate is as follows:

| Signal | Interpretation |
|---|---|
| 1.22 (d, 3H) | —CH—CH₃ |
| 1.28 (t, 3H) | —CH₂—CH₃ |
| 1.66 (d, 3H) | C=CH—CH₃ |
| 3.44 (m, 1H) |  |
| 4.15 (q, 2H) | 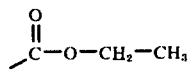 |
| 5.52 ppm (m, 2H) | —CH=CH— |

EXAMPLE XXVII

PREPARATION OF MIXTURE CONTAINING 80% CIS-n-HEXYL-2-METHYL-3-PENTENOATE AND 20% n-HEXYL-2-METHYL-2-PENTENOATE

Into a 125 ml reaction vessel equipped with magnetic stirrer, and maintained at room temperature, the following materials are added:

| (i) | Mixture of 80% cis-2-methyl-3-pentenoic acid and 20% 2-methyl-2-pentenoic acid prepared according to Example XXV | 1.1 g (0.01 moles) |
|---|---|---|
| (ii) | 1-Bromo hexane | 2.0 g (0.012 moles) |
| (iii) | Hexamethyl phosphoramide | 20 g |
| (iv) | Sodium hydroxide (50% aqueous solution | 1.0 g (0.012 moles) |

The reaction mass is stirred for a period of three hours at room temperature. It is then diluted with 100 ml of water and extracted with 50 ml of diethyl ether. The resulting ether extract is washed with three 10 ml portions of 20% aqueous sodium chloride solution. The ether is then evaporated to yield 2.0 g of an oil. GLC trapping gives cis-n-hexyl-2-methyl-3-pentenoate having an NMR analysis (CDCl₃) as follows:

| Signal | Interpretation |
|---|---|
| 0.90 (t, 3H) | CH₃—CH₂— |
| 1.24 (d, 3H) | CH₃—CH— |
| 1.28 (m, 6H) | —CH₂— |
| 1.64 (m, 5H) | —CH₂—C—O and =C—CH₃ |
| 3.44 (m, 1H) | —CH— |
| 4.08 (t, 2H) | —CH₂—O—C(=O) |
| 5.52 ppm (m, 2H) | —CH=CH— |

EXAMPLE XXVIII

FLAVOR FORMULATION CONTAINING MIXTURE OF 80% CIS-ETHYL-2-METHYL-3-PENTENOATE AND 20% ETHYL-2-METHYL-2-PENTENOATE

The following basic strawberry formulation is prepared:

| Ingredient | Parts by Weight |
| --- | --- |
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.1 |
| Gamma undecalactone | 0.2 |
| Diacetyl | 0.2 |
| Anethole | 0.1 |
| Cis-3-hexenol | 1.7 |
| 95% aqueous ethanol | 38.5 |
| Propylene glycol | 50.0 |
| | 100.0 |

To a portion of the foregoing formulation, 0.2% by weight of a mixture of 80% cis-ethyl-2-methyl-3-pentenoate and 20% ethyl-2-methyl-2-pentenoate prepared according to the process of Example XXVI is added. The formulation with the cis-ethyl-2-methyl-3-pentenoate is compared to the same formulation without said cis-ethyl-2-methyl-3-pentenoate.

Both flavors are evaluated in a milk beverage sweetened with 10% sugar at the rate of 100 ppm. Both beverages are tasted by an expert panel. The beverage containing the strawberry formulation with the addition of the mixture containing 80% cis-ethyl-2-methyl-3-pentenoate is unanimously preferred as having a more natural like, delicate strawberry aroma, a sweeter, more pleasant strawberry taste and a sweet, strawberry aftertaste.

EXAMPLE XXIX

RASPBERRY PERFUME FORMULATION

The following formulation is prepared:

| Ingredient | Parts by Weight |
| --- | --- |
| Mixture containing 80% cis-ethyl 2-methyl-3-pentenoate and 20% ethyl-2-methyl-2-pentenoate prepared according to the process of Example XXVI | 10 |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl Acetate | 50 |
| 4-(parahydroxyphenyl)-2-butanone | 50 |
| Ethyl laurate | 30 |
| Ethyl isovalerate | 10 |
| Ethyl butyrate | 50 |
| Cinnamyl cinnamate | 20 |
| | 419 |

The mixture containing the cis-ethyl-2-methyl-3-pentenoate imparts to this raspberry perfume formulation a delicate raspberry topnote nuance.

EXAMPLE XXX

TOBACCO FLAVOR FORMULATION AND TOBACCO

A tobacco mixture is produced by admixing the following materials:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the mixture containing 80% cis ethyl-2-methyl-3-pentenoate and 20% ethyl-2-methyl-2-pentenoate produced according to the process of Example XXVI. The control cigarettes not containing the mixture having 80% cis-ethyl-2-methyl-3-pentenoate produced according to the process of Example XXVI and the experimental cigarettes which do contain the mixture having 80% cis-ethyl-2-methyl-3-pentenoate produced according to the process of Example XXVI are evaluated by paired comparison, and the results are as follows:

In aroma, the cigarettes containing the mixture having 80% cis-ethyl-2-methyl-3-pentenoate have been found to be more aromatic.

In smoke flavor, the cigarettes containing the mixture having 80% cis-ethyl-2-methyl-3-pentenoate are more aromatic, more sweet, more bitter, slightly less harsh in the mouth and throat and leave a slight, sweet chemical mouth-coating effect similar to Turkish tobacco.

In summary, the mixture having 80% cis-ethyl-2-methyl-3-pentenoate enhances the tobacco-like taste and aroma of a blended cigarette and imparts to that cigarette a Turkish-like character in smoke flavor.

EXAMPLE XXXI

The following mixture is prepared:

| Ingredient | Parts by Weight |
| --- | --- |
| Ethyl acetoacetate | 3 |
| Ethyl laurate | 10 |
| Cinnamyl isobutyrate | 3 |
| Cinnamyl isovalerate | 5 |
| Diacetyl | 2 |
| Heliotropyl acetate | 20 |
| Peach aldehyde coeur | 100 |
| Ethyl butyrate | 200 |
| Ethyl isovalerate | 20 |

-continued

| Ingredient | Parts by Weight |
|---|---|
| Ethyl heptanoate | 1 |
| Dulcinyl | 5 |
| 2(para-hydroxyphenyl)-3-butanone | 2 |
| Ethyl acetate | 1 |
| Beta-ionone | 10 |
| Palatone | 2 |
| Ethyl vanillin | 1 |
| Ethyl-3-methyl-3-phenyl glycidate | 150 |
| Mixture containing 80% n-hexyl-2-methyl-cis-3-pentenoate (prepared according to the process of Example XXVII) | 5 |

The mixture containing 80% ethyl-2-methyl-cis-3-pentenoate isomer mixture prepared according to the process of Example XXVII imparts a fruity, chamomile, peppery, floral note to this strawberry fragrance.

EXAMPLE XXXII

PREPARATION OF SOAP COMPOSITION

One hundred grams of soap chips are mixed with one gram of the perfume composition of Example XXIX until a substantially homogeneous composition is obtained. The perfumed soap composition manifests an excellent raspberry character with a delicate raspberry topnote nuance.

EXAMPLE XXXIII

PREPARATION OF A DETERGENT COMPOSITION

A total of 100 g of a detergent powder is mixed with 0.15 g of the perfume composition of Example XXIX until a substantially homogeneous composition is obtained. This composition has an excellent raspberry fragrance.

EXAMPLE XXXIV

PREPARATION OF A COSMETIC POWDER COMPOSITION

A cosmetic powder is prepared by mixing in a ball mill 100 g of talcum powder with 0.25 g of the mixture containing 80% n-hexyl-2-methyl-cis-3-pentenoate prepared according to Example XXVII. It has an excellent fruity, chamomile aroma.

EXAMPLE XXXV

PERFUMED LIQUID DETERGENT

Concentrated liquid detergents with a fruity, chamomile odor are prepared containing 0.10%, 0.15% and 0.20% of the mixture having 80% n-hexyl-2-methyl-cis-3-pentenoate prepared according to Example XXVII. They are prepared by adding and homogeneously mixing the appropriate quantity of mixture containing 80% n-hexyl-2-methyl-cis-3-pentenoate in the liquid detergent. The detergents all possess a fruity, chamomile fragrance, the intensity increasing with greater concentration of mixture containing 80% n-hexyl-2-methyl-cis-3-pentenoate.

EXAMPLE XXXVI

PREPARATION OF A COLOGNE AND HANDKERCHIEF PERFUME

The composition of Example XXXI is incorporated in a cologne at a concentration of 2.5% in 85% aqueous ethanol; and into a handkerchief perfume at a concentration of 20% (in 95% aqueous ethanol). The use of the mixture containing 80% n-hexyl-2-methyl-cis-3-pentenoate in the composition of Example XXXI affords a distinct and definite strong strawberry aroma this a chamomile note to the handkerchief perfume and cologne.

EXAMPLE XXXVII

PREPARATION OF SOAP COMPOSITION

One hundred grams of soap chips are mixed with one gram of mixture containing 80% n-hexyl-2-methyl-cis-3-pentenoate of Example XXVII until a substantially homogeneous composition is obtained. The perfumed soap composition manifests an excellent raspberry aroma with fruity and green notes and a chamomile nuance.

EXAMPLE XXXVIII

PREPARATION OF A DETERGENT COMPOSITION

A total of 100 g of a detergent powder is mixed with 0.15 g of the mixture containing 80% ethyl-2-methyl-cis-3-pentenoate of Example XXVI until a substantially homogeneous composition is obtained. This composition has an excellent raspberry aroma with fruity and green notes and a chamomile nuance.

EXAMPLE XXXIX

PREPARATION OF ETHYL-2-METHYL-3,4-PENTADIENOATE

Reaction:

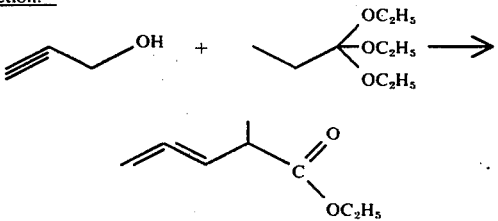

Into a 2 liter autoclave, the following materials are placed:

| Ingredient | Amount |
|---|---|
| Triethyl orthopropionate | 495 grams |
| 2-Propyn-1-ol | 90 grams |
| Propionic acid | 12 grams |

The autoclave is closed and the reaction mass is heated to 150° C. over a period of 50 minutes. The reaction mass is then maintained at a temperature of between 135°–160° C and at a pressure of 20 up to 60 psig for a period of 3 hours. At the end of this 3-hour period, the autoclave is cooled to room temperature and then opened. 12.6 g of sodium bicarbonate is then added to the reaction mass in order to neutralize the propionic acid. 30 g of Primol (see note 1) and 0.1 g of Ionol (see note 2) are added and the resulting reaction product is fractionally distilled at atmospheric pressure to a pot temperature of 129° C. A mixture of ethanol and ethyl propionate is distilled over. Vacuum is then applied to the distillation column and the resultant product, ethyl-2-methyl-3,4-pentadienoate is distilled at a vapor temperature of 65°–69° C at a pressure of 24–33 mm Hg as fractions 5–10 of the following fractions:

| Fraction No. | Vapor Temperature | Liquid Temperature | Pressure (mm Hg) | Weight of Fraction | Reflux Ratio |
|---|---|---|---|---|---|
| 1 | 68–72° C | 127–87° C | 760 | 174.5 g | 9:1 |
| 2 | 28–42 | 86–83 | 48–50 | 19.4 | 9:1 |
| 3 | 69 | 84 | 45 | 12.6 | 9:1 |
| 4 | 65 | 79 | 34 | 20.1 | 9:1 |
| 5 | 67 | 80 | 33 | 38.9 | 4:1 |
| 6 | 67 | 82 | 33 | 32.5 | 4:1 |
| 7 | 67 | 82 | 33 | 36.8 | 4:1 |
| 8 | 67 | 83 | 33 | 37.2 | 4:1 |
| 9 | 66 | 84 | 24 | 39.8 | 4:1 |
| 10 | 65 | 94 | 24 | 36.9 | 4:1 |
| 11 | 57 | 108 | 10 | 45.5 | 4:1 |
| 12 | 39 | 172 | 2.3 | 14.5 | 4:1 |

The resulting material is confirmed by IR, NMR and mass spectral analyses to have the structure:

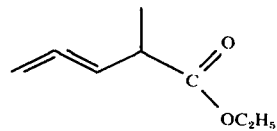

Mass spectral analysis:
Parent peak, then in order of decreasing intensity:
m/e = 140/ 67, 97, 29, 41, 125
Nuclear Magnetic Resonance Analysis:

| ppm | Interpretation | |
|---|---|---|
| 1.26 ppm (t) | $CH_3-C-O-C-$ with $\parallel O$ | ⎫ |
| 1.28 ppm (d) | $CH_3-C-C-$ with $\parallel O$ | ⎬ 6H |
| 3.10 ppm (m) | $=C-CH-C=O$ | 1H |
| 4.12 ppm (q) | $CH_3-CH_2-O-C-$ with $\parallel O$ | 2H |
| 4.76 ppm (m) | $H_2C=C=C-$ | 2H |
| 5.40 ppm (m) | $C=C=CH$ | 1H |

The nuclear magnetic resonance spectrum for fraction 10 is set forth in FIG. 1.
Infra Red Analysis for fraction 10:
Peaks:
850 cm$^{-1}$
1050
1175
1225
1375
1425
1730
1950
2880
2925
2975

Figure 2:
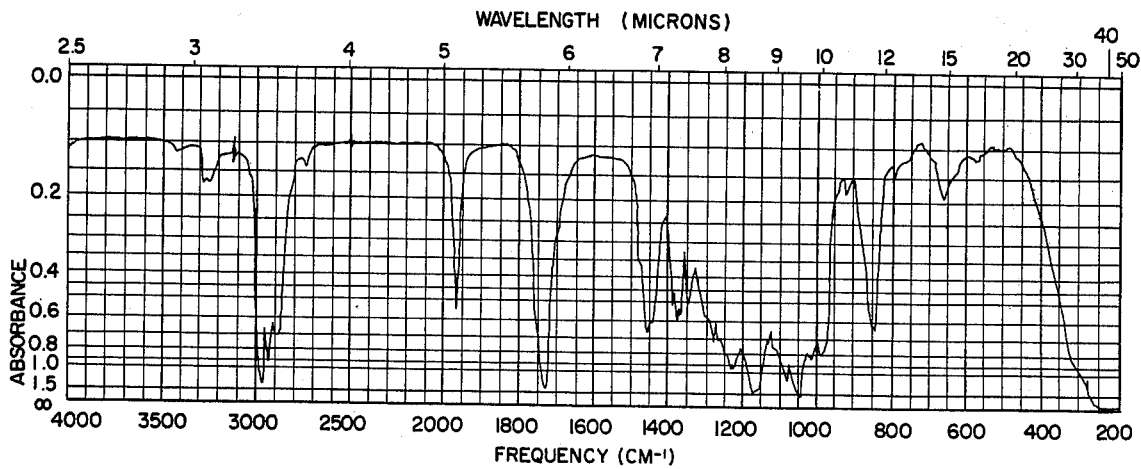

The infra-red spectrum is set forth in FIG. 2.

Note 1: Primol is a registered trademark indentifying a hydrocarbon mineral oil produced by Exxon Corp. of Linden, New Jersey.

Note 2: Ionol is a registered trademark identifying the compound 2,6-di-t-butyl-4-methyl phenol.

EXAMPLE XL

HYDROGENATION OF ETHYL-2-METHYL-3,4-PENTADIENOATE USING A 5% PALLADIUM-ON-CARBON CATALYST

Reaction:

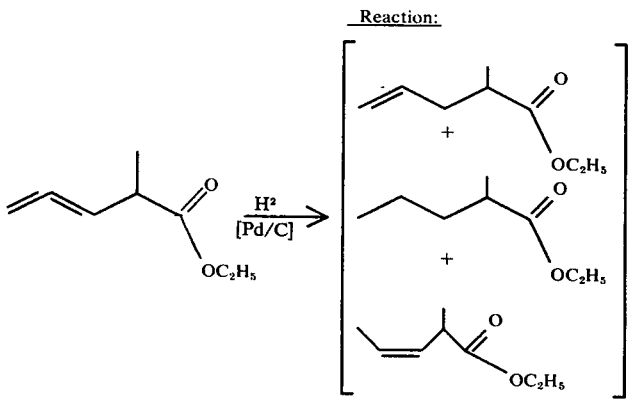

Into a 250 cc Parr Bomb, the following ingredients are placed:

| Ingredient | Amount |
|---|---|
| Ethyl-2-methyl-3,4-pentadienoate produced according to the process of Example I | 25 grams |
| 5% Palladium-on-carbon | 0.025 grams |

The Parr Bomb is connected by means of pressure tubing to a hydrogen-containing cylinder. The Parr Bomb is then sealed. Hydrogen is introduced from the hydrogen-containing cylinder and maintaining the pressure within the Parr Bomb at 25–50 ppsi. The reaction is maintained at room temperature using external cooling. After a period of 3.5 hours, the Parr Bomb is opened and the contents are filtered. GLC analysis indicates that the reaction is completed. GLC analysis (conditions: 8 ft. × ½ inch carbowax column; column temperature 120° C) indicates weight percentages of the following components:

| Component | Weight Percent |
|---|---|
| Ethyl-2-methyl-cis-3-pentenoate | 65.7% |
| Ethyl-2-methyl-4- | 14.3% |

| Component | Weight Percent |
| --- | --- |
| pentenoate Ethyl-2-methyl pentanoate | 19.9% |

The GLC spectrum is illustrated in FIG. 3.

EXAMPLE XLI

HYDROGENATION OF ETHYL-2-METHYL-3,4-PENTADIENOATE USING A LINDLAR CATALYST, THEREBY PREPARING MIXTURES OF ETHYL-2-METHYL-CIS-3-PENTENOATE

Reaction:

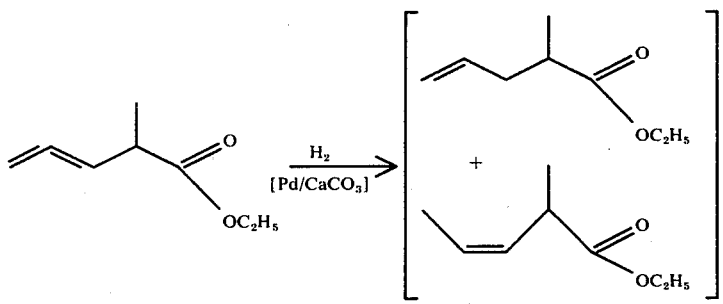

Into a 2-liter autoclave, the following ingredients are placed:

| Ingredient | Quantity |
| --- | --- |
| Ethyl-2-methyl-3,4-pentadienoate produced according to the process of Example I | 577.8 grams |
| 5% Palladium-on-calcium carbonate catalyst (Lindlar catalyst) | 1.4 grams |

The autoclave is connected by means of pressure tubing to a hydrogen-containing cylinder. The autoclave is then sealed. Hydrogen is introduced into the autoclave from the hydrogen-containing cylinder and maintaining the pressure within the autoclave at 60 pounds per square inch gauge the reaction mass is stirred. During the hydrogenation and over a 19-hour period, the reaction mass is maintained at room temperature by means of the application of cooling. At the end of the 19-hour period, the autoclave is opened; and an additional 1.4 grams of Lindlar catalyst is added. The autoclave is then closed and hydrogen is continuously added thereto while stirring the reaction mass over an additional reaction period of 10 hours. At the end of the 10-hour period, the autoclave is opened, and the reaction mass if filtered. An additional 2.8 grams of Lindlar catalyst is then added to the reaction mass which is then again placed in the autoclave with hydrogen being added thereto and pressure being maintained at 60 pounds per square inch gauge. At the end of one and three-quarter hours, GLC analysis indicates that the reaction is completed. The autoclave is then opened and the reaction mass is filtered. The filtered reaction mass is then distilled on a 1 inch × 1 ft. Goodloe distillation column after adding thereto 10 grams of Primol (see Note 1 ) and 0.1 grams of Ionol (see Note 2) yielding the following fractions.

| Fraction No. | Vapor Temp. | Liquid Temp. | Vacuum (mm Hg) Pressure | Weight of Fraction | Reflex Ratio |
| --- | --- | --- | --- | --- | --- |
| 1 | 31–33° C | 77–86° C | 200–205 | 18.2 g | 19:1 |
| 2 | 60 | 90 | 200 | 17.0 | 19:1 |
| 3 | 61 | 93 | 200 | 11.0 | 19:1 |
| 4 | 62 | 97 | 200 | 12.6 | 19:1 |
| 5 | 62 | 100 | 200 | 13.6 | 19:1 |
| 6 | 62 | 107 | 200 | 13.5 | 19:1 |
| 7 | 62 | 111 | 200 | 14.3 | 19:1 |
| 8 | 65 | 115 | 200 | 12.5 | 19:1 |
| 9 | 81 | 119 | 200 | 13.1 | 19:1 |
| 10 | 88–110 | 116–117 | 205 | 6.6 | 19:1 |
| 11 | 112 | 117 | 205 | 6.0 | 19:1 |
| 12 | 113 | 117 | 205 | 6.2 | 19:1 |
| 13 | 113 | 118 | 205 | 7.0 | 19:1 |
| 14 | 114 | 118 | 205 | 4.5 | 19:1 |
| 15 | 114 | 118 | 205 | 17.8 | 9:1 |
| 16 | 114 | 118 | 205 | 21.5 | 9:1 |
| 17 | 114 | 118 | 205 | 23.9 | 9:1 |
| 18 | 114 | 118 | 205 | 21.2 | 9:1 |
| 19 | 115 | 120 | 205 | 24.5 | 9:1 |
| 20 | 115 | 120 | 205 | 23.2 | 9:1 |
| 21 | 115 | 120 | 205 | 10.0 | 9:1 |
| 22 | 114–115 | 119–120 | 200–205 | 20.8 | 9:1 |
| 23 | 115 | 121 | 205 | 20.8 | 9:1 |
| 24 | 115 | 121 | 205 | 15.0 | 9:1 |
| 25 | 115 | 122 | 205 | 19.3 | 9:1 |
| 26 | 115 | 124 | 205 | 17.9 | 9:1 |
| 27 | 116 | 125 | 205 | 21.9 | 9:1 |
| 28 | 116 | 128 | 205 | 18.9 | 9:1 |
| 29 | 116 | 131 | 205 | 19.0 | 4:1 |
| 30 | 116 | 144 | 205 | 24.6 | 4:1 |
| 31 | 116 | 160 | 205 | 13.5 | 4:1 |
| 32 | 111 | 200 | 205 | 6.1 | 4:1 |

Fractions 12–31 are bulked.

Fractions 12, 13, 14, 21, 23 and 31 are analyzed using GLC analysis (conditions: 10 feet × ¼ inch Carbowax 20M column programmed at 120° C–150° C).

| Fraction No. | Weight of Fraction | Percentage ethyl-2-methyl-cis-3-pentenoate | Percentage ethyl-2-methyl-4-pentenoate |
| --- | --- | --- | --- |
| 12 | 6.2 g | 57.6% | 41.6% |
| 13 | 7.0 g | 59.2% | 38.9% |
| 21 | 10.0 g | 70.9% | 28.7% |
| 23 | 20.8 g | 75.6% | 24.1% |
| 31 | 13.5 g | 93.8% | 4.9% |

The GLC curve for Fraction No. 23 is set forth in FIG. 4.

Analyses:
a. Ethyl-2-methyl-cis-3-pentenoate
  i. Mass Spectral Analysis: Parent Peak; then in decreasing order of intensity: m/e = 142 ($M^+$); 69, 41, 29, 27, 39, 68.

ii. NMR Analysis:

| ppm | Interpretation | |
|---|---|---|
| 1.18 (d) | =C–C(CH₃)–C=O, CH₃–C–O | 2H |
| 1.22 (t) | | |
| 1.64 (d) | =C–CH₃ | 3H |
| 3.40 (m) | =C–C(H)–C=O | 1H |
| 4.10 (q) | –CH₂–O–C(=O)– | 2H |
| 5.20 (m) | HC=CH | 2H |

Infrared Analysis:
710, 860, 960, 1020, 1045, 1090, 1140, 1175, 1240, 1325, 1370, 1395, 1450, 1650, 1730, 2880, 2900, 2940, 2980, 3020 cm$^{-1}$ b. Ethyl-2-methyl-4-pentenoate
Mass spectral analysis: Parent peak then in decreasing order of intensity, m/e = 142/69, 41, 29, 27, 39, 68. NMR Analysis:

| ppm | Interpretation | |
|---|---|---|
| 1.12 (d) | CH₃–C–C, CH₃–C–O | 6H |
| 1.21 (t) | | |
| 2.60 – 2.06 (m) | methine and methylene protons | 3H |
| 4.10 (q) | CH₃–CH₂O–C(=O)– | 2H |
| 5.10 – 4.94 | HC=CH₂ | 2H |
| 5.94 – 5.03 | HC=CH₂ | 1H |

Infrared Analysis:
910, 990, 1025, 1050, 1090, 1140, 1180, 1250, 1275, 1345, 1370, 1430, 1640, 1730, 2880, 2900, 2940, 2980 cm$^{-1}$ Note 1: Primol is a registered trademark identifying a hydrocarbon mineral oil produced by Exxon Incorporation of Linden, New Jersey.

Note 2: Ionol is a registered trademark identifying the compound 2,6-di-tert-butyl-4-methylphenol.

EXAMPLE XLII

HYDROGENATION OF ETHYL-2-METHYL-3,4-PENTADIENOATE USING A RANEY NICKEL CATALYST THEREBY PREPARING MIXTURES OF ETHYL-2-METHYL-CIS-3-PENTENOATE AND ETHYL-2-METHYL PENTANOATE

Reaction:

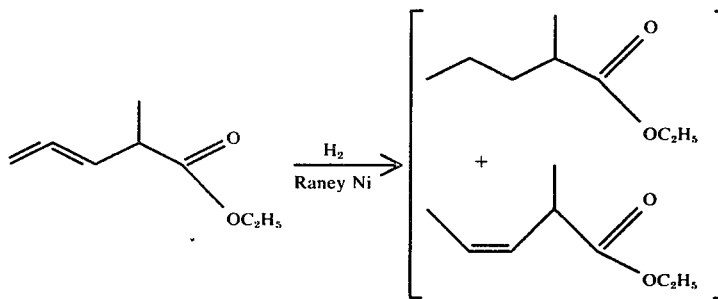

Into a 2-liter autoclave fitted by means of pressure tubing to a hydrogen-containing cylinder is added the following materials:

| Ingredient | Quantity |
|---|---|
| Ethyl-2-methyl-3,4-pentadienoate prepared according to the process of Example XXXIX | 283.3 g |
| Raney nickel | 14 g |

Figure 5:
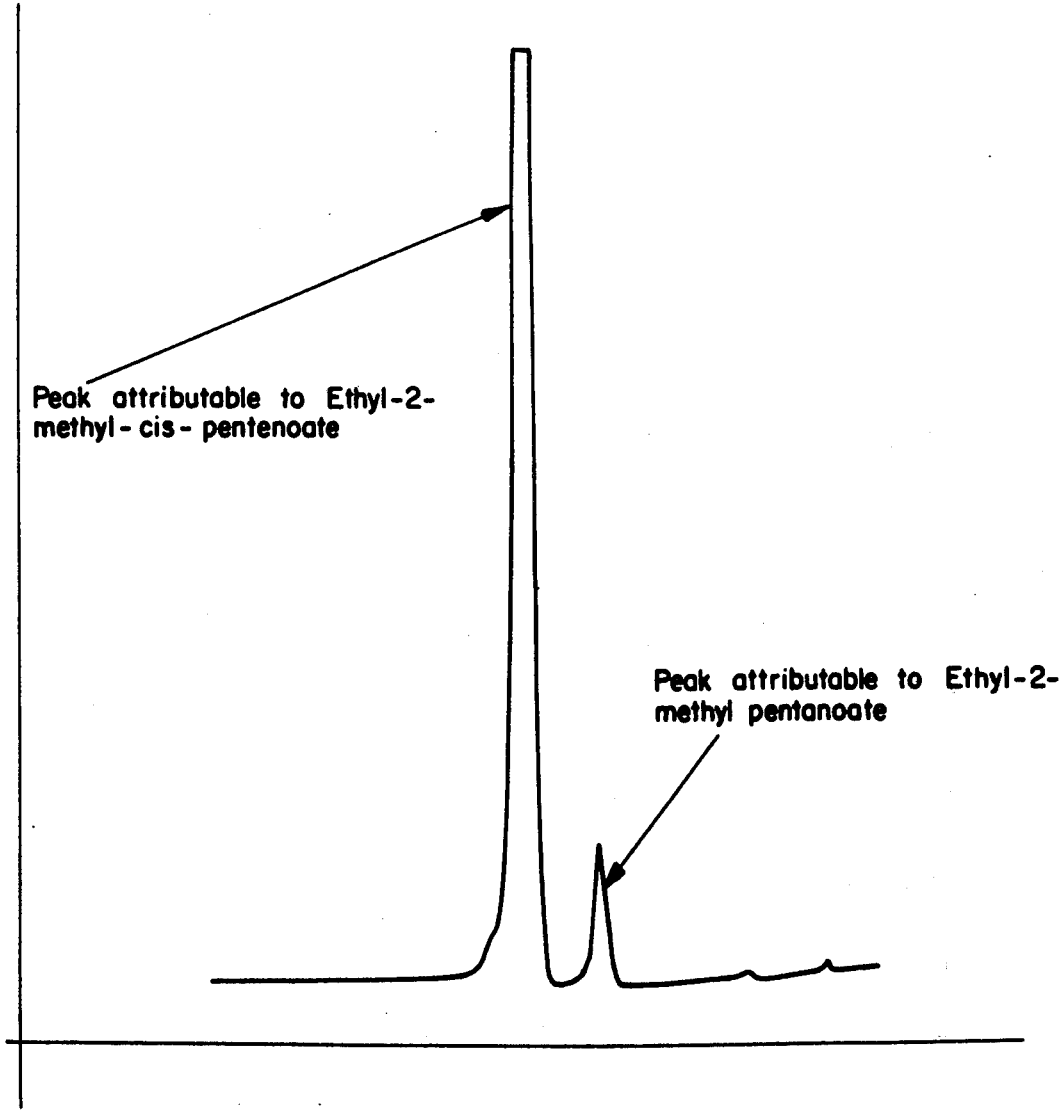

The autoclave is closed and, while stirring and maintaining the temperature at 20° C (using external cooling), the reaction mass is pressurized to 20 pounds per square inch gauge (psig) using hydrogen. The pressure is maintained using the hydrogen feed at 20 pounds per square inch and the temperature is maintained at 20° C over a period of 3 hours. At the end of the 3-hour period, the autoclave is opened and the reaction mass is filtered. GLC analysis indicates that the reaction is complete. According to GLC, NMR, IR and mass spectral analyses, the reaction mass contains 65% ethyl-2-methyl-cis-3-pentenoate and 35% ethyl-2-methylpentanoate. The GLC curve is set forth in FIG. 5.

After adding 5.0 grams of Primol and 0.1 grams of Ionol the filtered reaction mass is distilled on a 36 inches × 1.5 inches Goodloe distillation column. The following fractions are collected:

| Fraction No. | Vapor Temp. | Liquid Temp. | Vacuum (mm Hg Pressure) | Weight of Fraction | Reflux Ratio |
|---|---|---|---|---|---|
| 1 | 50° C | 55° C | 20.0 | 7.4 g | 19:1 |
| 2 | 50 | 55 | 20.0 | 8.5 | 19:1 |
| 3 | 50 | 55 | 20.0 | 8.8 | 19:1 |
| 4 | 50 | 55 | 20.0 | 14.5 | 19:1 |
| 5 | 50 | 55 | 20.0 | 15.9 | 19:1 |
| 6 | 50 | 55 | 20.0 | 11.4 | 19:1 |
| 7 | 50 | 55 | 20.0 | 12.5 | 19:1 |
| 8 | 50 | 55 | 20.0 | 11.5 | 19:1 |
| 9 | 50 | 55 | 20.0 | 11.7 | 19:1 |
| 10 | 50 | 55 | 20.0 | 11.2 | 19:1 |
| 11 | 50 | 55 | 20.0 | 22.2 | 19:1 |
| 12 | 50 | 55 | 20.0 | 11.0 | 19:1 |
| 13 | 50 | 55 | 20.0 | 11.8 | 19:1 |
| 14 | 50 | 55 | 20.0 | 12.7 | 19:1 |
| 15 | 52 | 56–57 | 20.0 | 10.0 | 19:1 |
| 16 | 52 | 57 | 20.0 | 10.9 | 19:1 |

-continued

| Fraction No. | Vapor Temp. | Liquid Temp. | Vacuum (mm Hg Pressure) | Weight of Fraction | Reflux Ratio |
|---|---|---|---|---|---|
| 17 | 52 | 57 | 20.0 | 9.5 | 19:1 |
| 18 | 52 | 57 | 20.0 | 7.0 | 19:1 |
| 19 | 52 | 57 | 20.0 | 3.7 | 19:1 |
| 20 | 53 | 58 | 20.0 | 2.6 | 19:1 |
| 21 | 53 | 58 | 20.0 | 5.8 | 19:1 |
| 22 | 53 | 59 | 20.0 | 5.5 | 19:1 |
| 23 | 53 | 63 | 20.0 | 6.0 | 19:1 |
| 24 | 53 | 95 | 20.0 | 7.5 | 19:1 |
| 25 | 53 | 140 | 20.0 | 3.8 | 19:1 |

Fractions 16–25 are bulked and GLC, NMR and IR analyses indicate that this bulked fraction contains 5.7% ethyl-2-methyl-pentanoate and 93.8% ethyl-2-methyl-cis-3-pentenoate. This material has a fresh strawberry taste with light, rubbery off-notes. When this fraction is re-distilled in order to eliminate the saturated ester which counter-acts the delicate strawberry taste of the unsaturated cis ester, the material is an excellent, fresh strawberry flavor additive. The 100% cis material has a fruity, strawberry, pineapple aroma with rum, and honey undertones suitable as a food flavor, perfumery, and tobacco flavor additive.

IR, NMR and mass spectral analyses for the saturated ester, the ethyl-2-methyl pentanoate is as follows:

Mass Spectral Analysis: Parent peak, then in order of decreasing intensity:
m/e = 144/43, 102, 29, 27, 71, 74.

NMR Analysis:

| ppm | Interpretation | |
|---|---|---|
| 0.88 (t) | $CH_3-(CH_2)_n-$ | 3H |
| 1.08 (d) | $CH_3-\overset{H}{\underset{\mid}{C}}-$ | 6H |
| 1.21 (t) | $CH_3-C-O-\overset{O}{\underset{\parallel}{C}}-$ | |
| 1.70–1.34 (m) | $-CH_2-$ | 4H |
| 2.40 (m) | $Me-\overset{H}{\underset{\mid}{C}}-$ | 1H |
| 4.08 (q) | $Me-CH_2-O-\overset{O}{\underset{\parallel}{C}}-$ | 2H |

Infrared Analysis:
740 cm$^{-1}$, 850, 1035, 1050, 1080, 1145, 1180, 1245, 1350, 1375, 1460, 1730, 2880, 2940, 2960.

The IR, NMR and mass spectral data for the unsaturated cis ester, ethyl-2-methyl-cis-3-pentenoate, is identical to that set forth in Example XLI.

EXAMPLE XLIII

PREPARATION OF ETHYL-2-METHYL-CIS-3-PENTENOATE: ETHYL-2-METHYL-4-PENTENOATE AND ETHYL-2-METHYL PENTANOATE BY HYDROGENATION OF 2-METHYL-3,4-PENTADIENOATE USING A RANEY NICKEL CATALYST

Reaction:

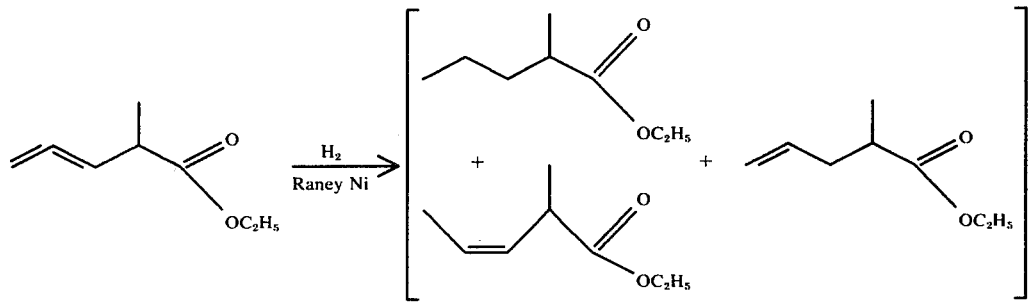

Into a 500 cc autoclave fitted by means of pressure tubing to a hydrogen-containing cylinder is added the following materials:

| Ingredient | Quantity |
|---|---|
| ethyl-2-methyl-3,4-pentadienoate prepared according to the process of Example XXXIX | 187 grams |
| Raney nickel | 7 grams |

The autoclave is closed, and, while stirring and maintaining the temperature at 20°–30° C (using external cooling) the reaction mass is pressurized to 50 pounds per square inch gauge (psig) using hydrogen. The pressure is maintained using the hydrogen feed at 50 pounds per square inch, and the temperature is maintained at 20°–30° C over a period of 5½ hours. After 2½ hours, 1 gm mole of hydrogen was absorbed in the reaction mass; and GLC analysis shows the presence of the following materials:

| | |
|---|---|
| ethyl-2-methyl pentanoate | 2% |
| ethyl-2-methyl-4-pentenoate | 25.7% |
| ethyl-2-methyl-cis-3-pentenoate | 62.5% |
| ethyl-2-methyl-3,4-pentadienoate | 8.9% (starting material) |

The reaction is continued for another hour by repressurization using the hydrogen feed up to 50 psig. At the end of the 3½ hours, 1.24 gm moles of hydrogen is absorbed by the reaction mass, and the autoclave is opened and again GLC analysis is carried out. GLC analysis indicates the following composition in the reaction mass after 3½ hours:

| | |
|---|---|
| ethyl-2-methyl-pentanoate | 11% |

| | |
|---|---|
| ethyl-2-methyl-4-pentenoate | 19.7% |
| ethyl-2-methyl-cis-3-pentenoate | 68% |

The autoclave is then closed and repressurized with hydrogen to 50 psig and the reaction is continued for another 2 hours, at which time 1.5 gm moles of hydrogen (total) is absorbed by the reaction mass. At the end of the 2 hour period, the autoclave is again opened and GLC analysis indicates the following:

| | |
|---|---|
| ethyl-2-methyl-pentenoate | 35% |
| ethyl-2-methyl-cis-3-pentenoate | 65% |

At the 5 ½ hour reaction time, it is significant to note that no ethyl-2½-methyl-4-pentenoate is present in the reaction mass.

Figure 6:
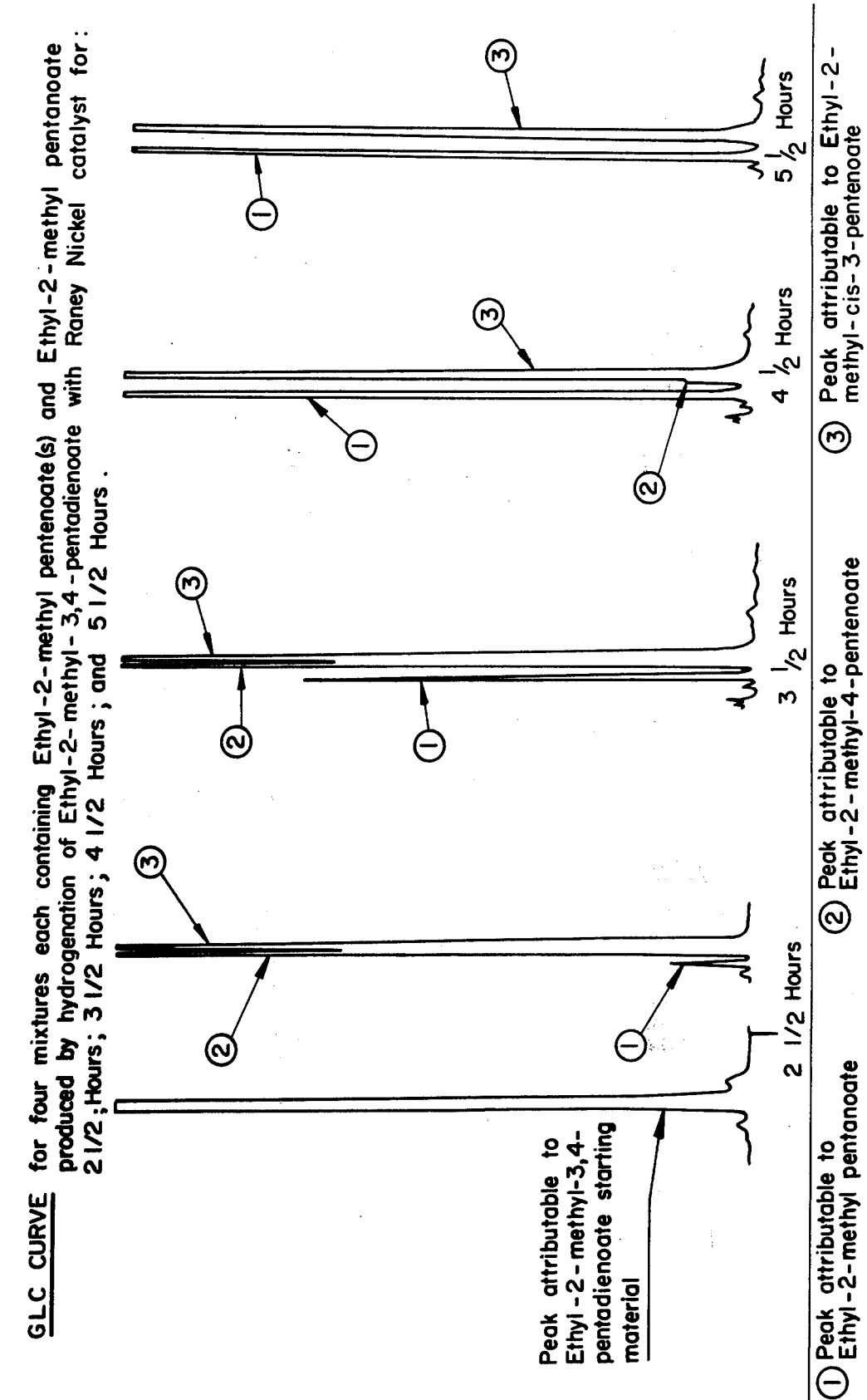

GLC analysis at 2½ hours, 3½ hours and 5½ hours are set forth in FIG. 6.

The final mixture is filtered and distilled in a 36 inches × 1½ inches Goodloe column after adding thereto 5.0 grams of Primol and 0.1 grams of Ionol yielding the following fractions:

| Fraction No. | Vapor Temp. | Liquid Temp. | Pressure (mm Hg) | Weight | Reflux Ratio |
|---|---|---|---|---|---|
| 1 | 50° C | 55° C | 20.0 | 7.4 | 19:1 |
| 2 | 50 | 55 | 20.0 | 8.5 | 19:1 |
| 3 | 50 | 55 | 20.0 | 8.8 | 19:1 |
| 4 | 50 | 55 | 20.0 | 14.5 | 19:1 |
| 5 | 50 | 55 | 20.0 | 15.9 | 19:1 |
| 6 | 50 | 55 | 20.0 | 11.4 | 19:1 |
| 7 | 50 | 55 | 20.0 | 12.5 | 19:1 |
| 8 | 50 | 55 | 20.0 | 11.5 | 19:1 |
| 9 | 50 | 55 | 20.0 | 11.7 | 19:1 |
| 10 | 50 | 55 | 20.0 | 11.2 | 19:1 |
| 11 | 50 | 55 | 20.0 | 22.2 | 19:1 |
| 12 | 50 | 55 | 20.0 | 11.0 | 19:1 |
| 13 | 50 | 55 | 20.0 | 11.8 | 19:1 |
| 14 | 50 | 55 | 20.0 | 12.7 | 19:1 |
| 15 | 52 | 56–57 | 20.0 | 10.0 | 19:1 |
| 16 | 52 | 57 | 20.0 | 10.9 | 19:1 |
| 17 | 52 | 57 | 20.0 | 9.5 | 19:1 |
| 18 | 52 | 57 | 20.0 | 7.0 | 19:1 |
| 19 | 52 | 57 | 20.0 | 3.7 | 19:1 |
| 20 | 53 | 58 | 20.0 | 2.6 | 19:1 |
| 21 | 53 | 58 | 20.0 | 5.8 | 19:1 |
| 22 | 53 | 59 | 20.0 | 5.5 | 19:1 |
| 23 | 53 | 63 | 20.0 | 6.0 | 19:1 |
| 24 | 53 | 95 | 20.0 | 7.5 | 19:1 |
| 25 | 53 | 140 | 20.0 | 3.8 | 19:1 |

Fraction No. 22 is analyzed using NMR, GLC and mass spectral analysis as being 95% ethyl-2-methyl-cis-3-pentenoate and 5% ethyl-2-methyl pentanoate. This fraction is then redistilled in order to substantially eliminate the saturated ester which counteracts the delicate strawberry taste of the unsaturated "cis" ester. The resulting "cis" ester is an excellent, fresh strawberry additive having a fruity, strawberry, pineapple aroma with rum and honey undertones suitable as a food flavor, medicinal product flavor, chewing gum flavor, perfumery adjuvant and tobacco additive. The IR, NMR and mass spectral data for the saturated and for the unsaturated esters are identical to those set forth in Examples XL and XLI supra.

When the above process is repeated without sampling for GLC analysis at the 2½ hour and 3½ hour intervals, after 5½ hours, 1.48 gm moles of hydrogen is absorbed in the reaction mass and GLC analysis shows the following:

| | |
|---|---|
| ethyl-2-methyl pentanoate | 38% |
| ethyl-2-methyl-cis-3-pentenoate | 61.4% |

When the above procedure is repeated with sampling at 3½ hours and 4 hours, the following results are obtained:

i. 3½ hours:

hydrogen uptake 1.4 gm moles percentage of ethyl-2-methyl-pentanoate is 27% percentage of ethyl-2-methyl-4-pentenoate is 4% ethyl-2-methyl-cis-3-pentenoate 68% ii. 4 hours:

hydrogen uptake 1.5 gm moles percentage ethyl-2-methyl pentanoate is 36% percentage ethyl-2-methyl-cis-3-pentenoate is 63.6%.

EXAMPLE XLIV

A. PREPARATION OF TRIHEXYL-ORTHOPROPIONATE

Reaction:

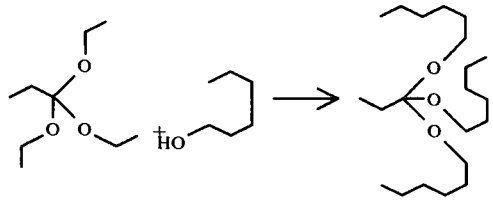

Into a three-liter distillation flask, equipped with a 2 inches splash column, reflux condenser and fraction cutter, the following materials are placed:

| Ingredients | Amount |
|---|---|
| Triethyl ortho propionate | 528 g (3 moles) |
| n-Hexyl alcohol | 1530 g (15 moles) |
| p-Toluene sulfonic acid | 3.4 g (0.02 moles) |
| Primol | 20 g |

The reaction mass is heated to a pot temperature of 150° C at atmospheric pressure and 398.9 g of "light" fractions distills off. The reaction mass is then placed under vacuum and the reaction product is distilled over as a colorless liquid at 1.3 mm Hg pressure and a temperature of 140°–171° C. The yield is 930.7 g (87.6%) and the product is a compound having the structure:

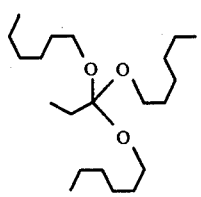

B. PREPARATION OF n-HEXYL-2-METHYL-3,4-PENTADIENOATE Reaction:

Reaction:

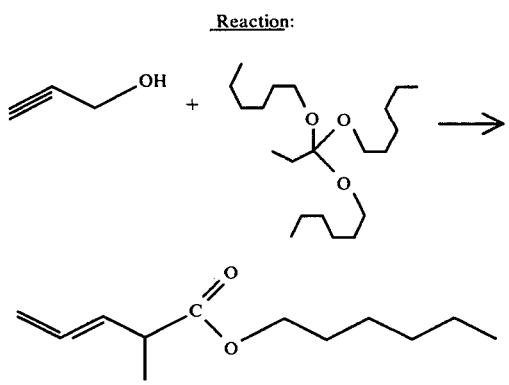

Into a 2-liter autoclave, the following materials are placed:

| Ingredient | Amount |
|---|---|
| n-Hexyl orthopropionate (produced according to the process of Part A) | 1240 grams (3.5 moles) |
| 2-Propyn-1-ol | 196 grams (3.5 moles) |
| Propionic acid | 30 grams |

The autoclave is closed and the reaction mass is heated to 120°–130° C (a heatup time of 50 minutes). The reaction mass is maintained at a temperature of between 120°–130° C for a period of 5 hours. At the end of this 5-hour period, the autoclave is cooled to room temperature. The reaction mixture is decanted and 35 g of sodium bicarbonate is then added to the reaction mass in order to neutralize the propionic acid. 40 g of Primol is added and the resulting reaction product is distilled. Fractions 6, 7 and 8 distilling 95°–101° C and 2.2–2.5 mm Hg (to yield 481.3 g of a crude product) are combined and fractionally distilled on a 12 × 1 inches Goodloe column after adding thereto 10.0 g Primol and 0.1 g Ionol, as follows:

| Fraction No. | Vapor Temp. | Liquid Temp. | Pressure (mm Hg) | Weight of Fraction | Reflux Ratio |
|---|---|---|---|---|---|
| 1 | 44 | 72–87 | 3.5–3.4 | 40.0 g | 9:1 |
| 2 | 47 | 97 | 3.4 | 33.9 | 9:1 |
| 3 | 77 | 101 | 3.4 | 36.5 | 9:1 |
| 4 | 88 | 104 | 3.4 | 20.3 | 9:1 |
| 5 | 89 | 104 | 3.4 | 33.9 | 9:1 |
| 6 | 89 | 104 | 3.4 | 29.1 | 9:1 |
| 7 | 80–89 | 105–115 | 3.5–3.4 | 33.5 | 9:1 |
| 8 | 89 | 115 | 3.2 | 33.4 | 9:1 |
| 9 | 89 | 117 | 3.1 | 84.1 | 3:1 |
| 10 | 90 | 119 | 3.2 | 83.6 | 3:1 |
| 11 | 86–89 | 110–112 | 3.2 | 32.5 | 9:1 |
| 12 | 89 | 125 | 3.2 | 74.4 | 3:1 |
| 13 | 88 | 155 | 3.3 | 32.4 | 3:1 |
| 14 | 110 | 195 | 3.3 | 44.5 | 3:1 |

Fractions 9 and 10 are bulked and the resulting material is confirmed by IR, NMR and mass spectral analyses to have a purity greater than 99% and to have the structure:

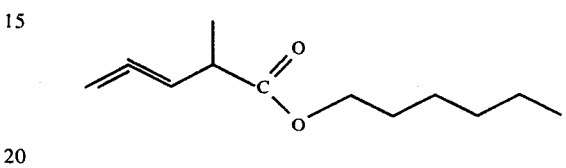

It has a tagette-oil-like, apple taste and aroma with pear and fatty nuances.

Figure 7:
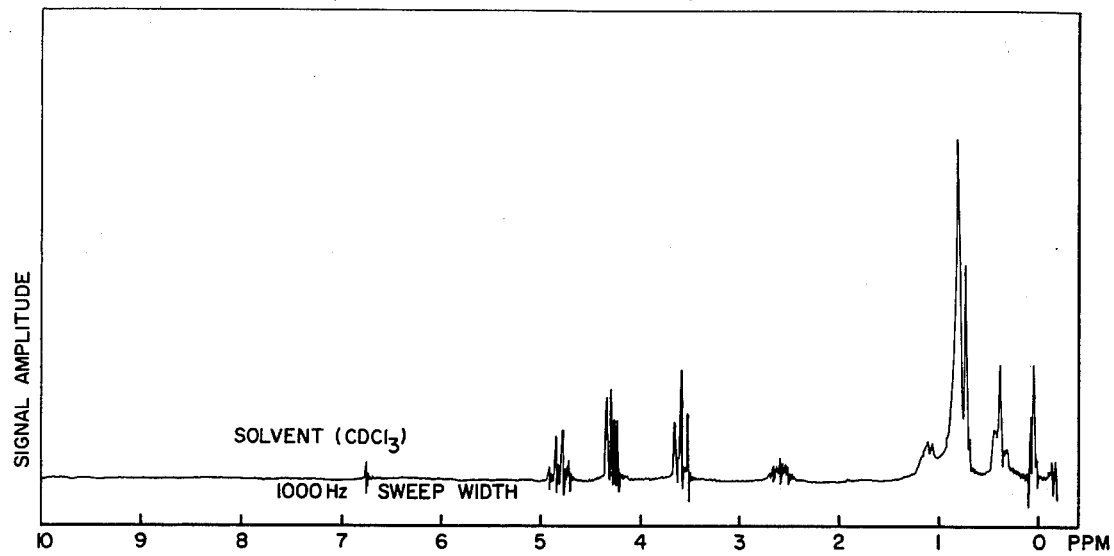
Figure 8:
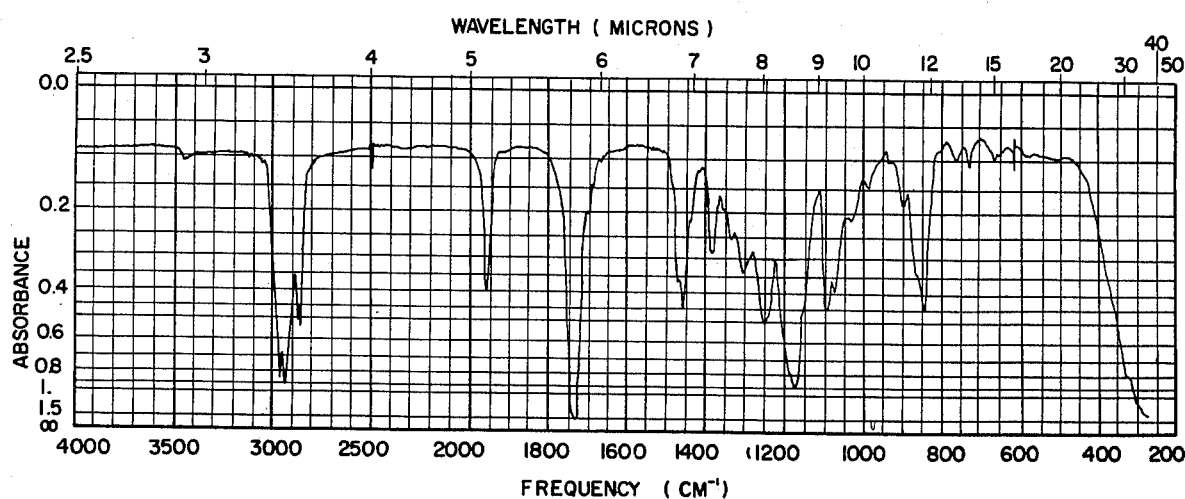

Analyses:
1. The nuclear magnetic resonance spectrum is illustrated in FIG. 7.
2. The infrared spectrum is illustrated in FIG. 8.
3. Mass spectral analysis: Molecular ion; then in order of decreasing intensity: 196/43, 41, 112, 97, 67, 85.
4. NMR analysis:

| ppm | Interpretation | |
|---|---|---|
| 0.88 ppm (t) | $CH_3-CH_2-$ | 3H |
| 1.24 ppm (d) | $CH_3-\overset{\overset{C=}{\|}}{\underset{\underset{C=O}{\|}}{C}}-$ | |
| 1.28 (broad s) | $-CH_2-$ | 11H |
| 1.62 (m) | $-CH_2-C-O-$ | |
| 3.10 (m) | $=C-\overset{H}{\underset{\|}{C}}-C=O$ | |
| 4.08 (t) | $-CH_2-O-\overset{\overset{O}{\|}}{C}$ | 2H |
| 4.76 (7 doublets) | $H_2C=C=C-\left\{\begin{array}{l}J=3Hz\\6Hz\end{array}\right\}$ | 2H |
| 5.32 (q) | $-C=C=CH$ | 1H |

5. Infrared analysis:
845 cm⁻¹
1065
1085
1175
1250
1455
1730
1960
2860
2880
2940
2960

EXAMPLE XLV

HYDROGENATION OF n-HEXYL-2-METHYL-3,4-PENTADIENOATE USING A LINDLAR CATALYST THEREBY PREPARING MIXTURES OF n-HEXYL-2-METHYL CIS-3-PENTENOATE: n-HEXYL-2-METHYL-4-PENTENOATE

Reaction:

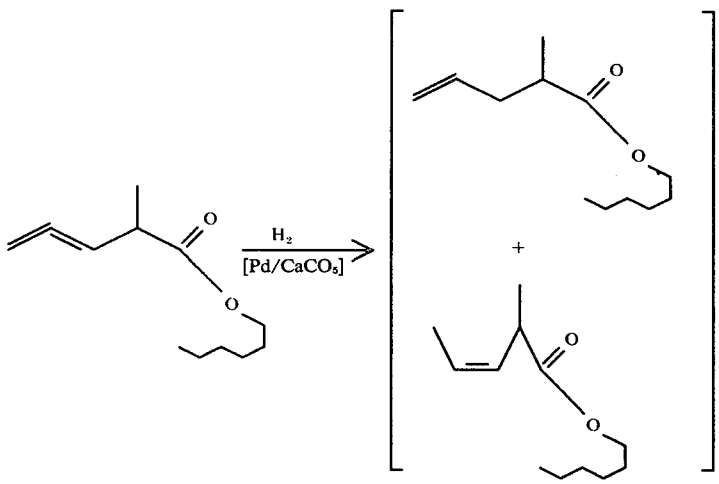

Into a 2-liter autoclave, the following ingredients are placed:

| Ingredient | Quantity |
|---|---|
| n-hexyl-2-methyl-3,4-pentadienoate produced according to the process of Example XLIV | 98 grams (0.5 moles) |
| palladium-on-calcium catalyst (Lindlar catalyst) | 1.0 grams |

The autoclave is connected by means of pressure tubing to a hydrogen-containing cylinder. The autoclave is then sealed, and while adding hydrogen into the autoclave from the hydrogen-containing cylinder and maintaining the pressure within the autoclave at 50 psig, the reaction mass is stirred. During the hydrogenation and over a period of 40 minutes. At the end of the 40-minute period, the autoclave is opened, and the reaction mass is filtered. GLC analysis shows total conversion to n-hexyl-2-methyl-cis-3-pentenoate and n-hexyl-2-methyl-4-pentenoate. The GLC curve is set forth in FIG. 9.

EXAMPLE XLVI

PREPARATION OF ISOBUTYL-2-METHYL-3,4-PENTADIENOATE

Reaction:

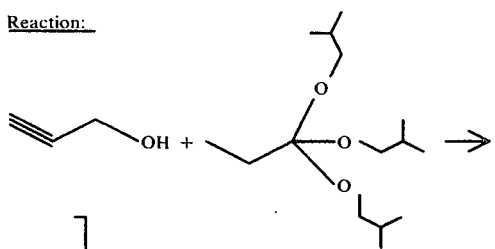

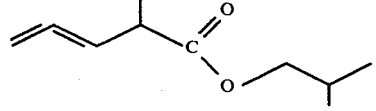

Into a 2 liter autoclave, the following materials are placed:

| Ingredient | Amount |
|---|---|
| Triisobutyl orthopropionate | 696.9 grams |
| 2-Propyn-1-ol | 151 grams |
| Propionic acid | 17 grams |

The autoclave is closed and the reaction mass is heated to 140° C over a period of 50 minutes. The reaction mass is then maintained at a temperature of 140° C for a period of 4 hours. At the end of this 4-hour period, the autoclave is cooled to room temperature. 20 g of sodium bicarbonate is then added to the reaction mass in order to neutralize the propionic acid. 30 g of Primol is added and the reaction mass is fractionally distilled on a 2 inch splash column yielding the following fractions:

| Fraction No. | Vapor Temperature | Liquid Temperature | Pressure (mm Hg) | Weight of Fraction | %Product |
|---|---|---|---|---|---|
| 1 | 38–25° C | 45–27° C | 30–8.7 | 182.1 | 2 |
| 2 | 30 | 44 | 6.0 | 192.5 | 4.1 |
| 3 | 70 | 77 | 6.0 | 55.4 | 14.6 |
| 4 | 72 | 80 | 6.8 | 213.9 | 93.3 |
| 5 | 72 | 200 | 7.9 | 131.6 | 97 |

10 g Primol and 0.1 g Ionol are then added to the resulting distillate which is vacuum distilled yielding isobutyl-2-methyl-3,4-pentadienoate as follows:

| Fraction No. | Vapor Temperature | Liquid Temperature | Pressure (mm Hg) | Weight of Fraction | Reflux Ratio |
|---|---|---|---|---|---|
| 1 | 41–70° C | 77–83° C | 7.3–7.7 | 15.4 | 19:1–19:1 |
| 2 | 72 | 78 | 7.9 | 12.9 | 19:1 |
| 3 | 72 | 78 | 7.8 | 15.1 | 19:1 |
| 4 | 72 | 78 | 7.8 | 22.8 | 9:1 |
| 5 | 72 | 78 | 7.8 | 30.3 | 4:1 |
| 6 | 72 | 78 | 7.8 | 39.6 | 4:1 |
| 7 | 72 | 78 | 7.8 | 48.3 | 4:1 |
| 8 | 72 | 78 | 7.8 | 47.3 | 4:1 |
| 9 | 72 | 78 | 7.8 | 46.0 | 4:1 |
| 10 | 72 | 81 | 7.8 | 43.6 | 4:1 |
| 11 | 72 | 204 | 7.8 | 7.7 | 4:1 |

Fractions 4–10 are bulked and the resulting material (greater than 99% purity via GLC) is confirmed by NMR and IR analyses to have the structure:

Nuclear Magnetic Resonance Analysis:

| ppm | Interpretation | |
|---|---|---|
| 0.92 ppm (d) | CH₃\\H/C— /CH₃ | 6H |
| 1.26 ppm (d) | CH₃—CH, C=C, C=O | 3H |
| 1.92 ppm (m) | H₃C\\H/C— /H₃C | 1H |
| 3.12 ppm (m) | O=C—C(H)—C=C | 1H |
| 3.87 ppm (d) | —CH₂—O—C(=O)— | 2H |
| 4.79 ppm (d of d)* *doublet of doublet | H₂C=C=C—C | 2H |
| 5.33 ppm (q) | H₂C=C=C(H)—C | 1H |

Figure 10:
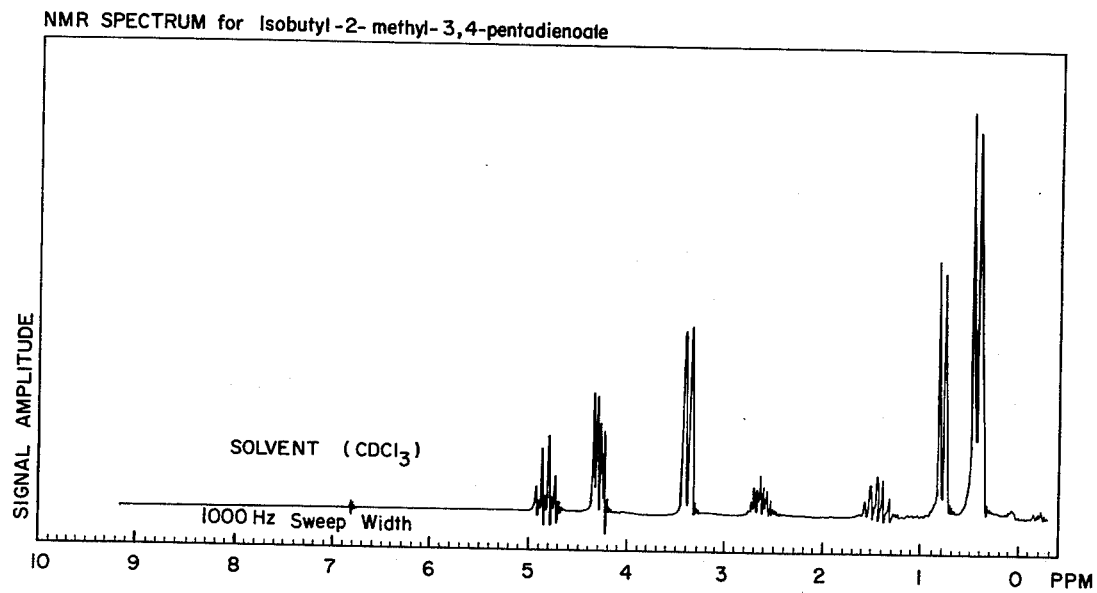

The nuclear magnetic resonance spectrum is set forth in FIG. 10.

Mass Spectral Data
168/ 41, 67, 57, 39, 29, 112, 97
Infra Red Analysis:
Peaks
840 cm⁻¹
985
1030
1065
1085
1170
1240
1300
1365
1375
1455
1470
1730
1955
2870
2940
2960

Figure 11:
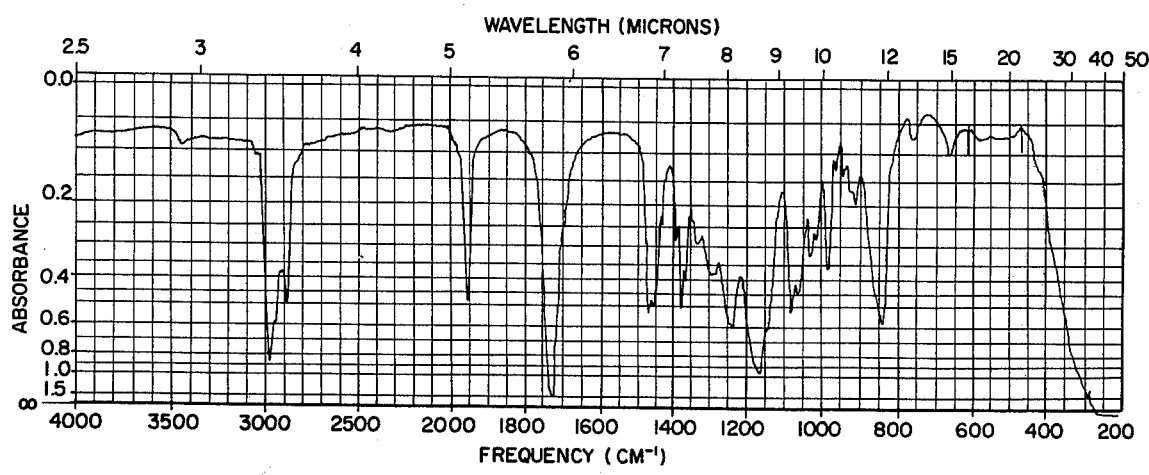

The infra-red spectrum is set forth in FIG. 11.

EXAMPLE XLVII

HYDROGENATION OF ISOBUTYL-2-METHYL-3,4-PENTADIENOATE USING A LINDLAR CATALYST THEREBY PREPARING MIXTURES OF ISOBUTYL-2-METHYL-CIS-3-PENTENOATE AND ISOBUTYL-2-METHYL-4-PENTENOATE

Reaction:

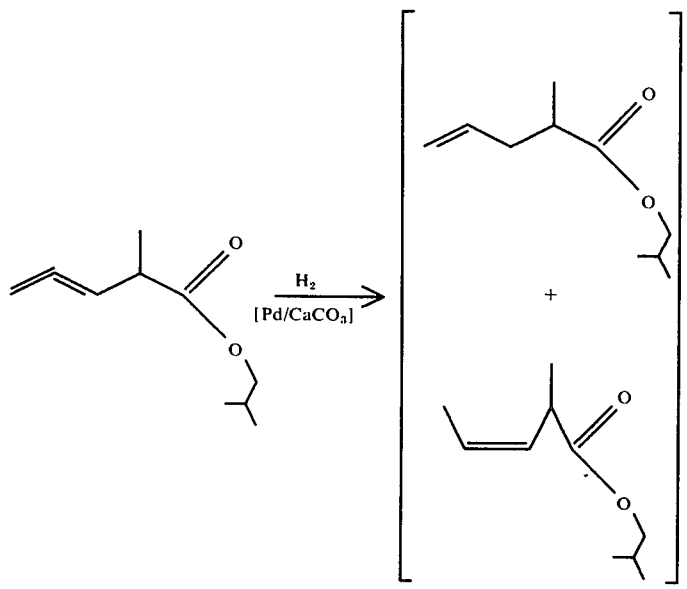

Into a 2-liter autoclave, the following ingredients are placed;

| Ingredient | Quantity |
|---|---|
| isobutyl-2-methyl-3,4-pentadienoate produced according to the process of Example XLVI | 168 grams |
| palladium-on-calcium carbonate catalyst (Lindlar catalyst) | 2.0 grams |

The autoclave is connected by means of pressure tubing to a hydrogen-containing cylinder. The autoclave is then sealed and while adding hydrogen into the autoclave from the hydrogen-containing cylinder and maintaining the pressure within the autoclave at 45–50 psig, the reaction mass is stirred. The hydrogenation takes place over a one-hour period. At the end of the one-hour period, the autoclave is opened and the reaction mass is filtered. GLC analysis indicates that all of the material is converted to a mixture of isobutyl-2-methyl-4-pentenoate and isobutyl-2-methyl-cis-3-pentenoate. The GLC analysis is illustrated in FIG. 12. The resulting material is confirmed by NMR. IR and MS analyses to have the following structures:

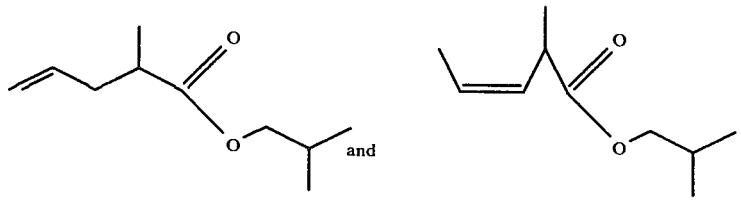

Nuclear Magnetic Resonance Analysis:

| ppm | Interpretation |
|---|---|
| 0.88 | $\text{CH}_3\text{-CH(H)-CH}_3$ group |
| 1.20 | $\underline{CH_3}-\overset{H}{\underset{|}{C}}-C=O$ with $C=C$ |
| 1.64 | $\underline{CH_3}-\overset{H}{C}=\overset{|}{C}-$ |
| 1.91 | $HC-\overset{O}{\underset{\|}{C}}-$ |
| 3.44 | $=C-\overset{H}{C}-\overset{O}{\underset{\|}{C}}-$ |
| 3.84 | $-CH_2-O-\overset{O}{\underset{\|}{C}}-$ |

-continued

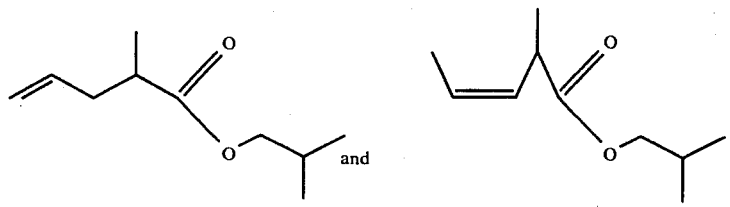 and

Nuclear Magnetic Resonance Analysis:

| ppm | Interpretation |
|---|---|
| 5.07 | $-\underset{|}{C}=\underline{CH_2}$ |
| 5.48 | $\underset{|}{H}\underline{C}=\underset{|}{C}H + \underset{|}{H}\underline{C}=\underset{|}{C}H_2$ |

IR Analysis (cm$^{-1}$)
990, 1015, 1020, 1040, 1170, 1240, 1325, 1375, 1465, 1725, 2280, 2960

MS Analysis
170/ 41, 69, 57, 29, 27, 39

EXAMPLE XLVIII

PREPARATION OF MIXTURE CONTAINING MAJOR PROPORTION OF ISOBUTYL-2-METHYL-CIS-3-PENTENOATE

Into a 500 ml reaction vessel equipped with stirrer, 3 inches splash column and thermometer, the following materials are added:

| | |
|---|---|
| Ethyl-2-methyl-cis-3-pentenoate containing mixture (produced according to Example XLI; bulked fractions 12-31) | 56 g (0.4 moles) |
| Isobutyl alcohol | 112 g |
| p-Toluene sulfonic acid | 0.5 g |
| Primol® | 10 g |
| Ionol® (A registered trademark for butylated hydroxytoluene manufactured by the Shell Chemical Company) | 0.1 g |

The reaction mass is heated to 110° C and atmospheric temperature for a period of 10 hours, while distilling off light fractions (head temperature: 45°–83° C). After the 10-hour period, 72.4 g light fractions are distilled.

Vacuum is then applied and the remaining unreacted isobutyl alcohol is distilled. The residual product is then rushed over yielding a mixture of isobutyl-2-methyl pentenoates and ethyl-2-methyl pentenoates. This mixture is refractionated through a 12 plate Vigreaux column at 95°–96° C and 40 mm Hg pressure yielding the isobutyl-2-methyl pentenoates:
  i. isobutyl-2-methyl-cis-3-pentenoate; and
  ii. isobutyl-2-methyl-4-pentenoate.

EXAMPLE XLIX

PREPARATION OF MIXTURE CONTAINING MAJOR PROPORTION OF n-Hexyl-2-METHYL-CIS-3-PENTENOATE Into a 250 ml reaction vessel equipped with stirrer, 3 inches splash column and thermometer, the following materials are added:

| | |
|---|---|
| Ethyl-2-methyl-cis-3-pentenoate containing mixture (prepared according to Example XLI; bulked fractions 12-31) | 56 g (0.4 moles) |
| n-Hexyl alcohol | 60 g |
| p-Toluene sulfonic acid | 0.4 g |
| Primol® | 10 g |
| Ionol® | 0.1 g |

The reaction mass is heated to 140°–150° C at atmospheric pressure over a period of 18 hours, while distilling off light fractions. By the end of the 18-hour period, 11.7 g of low boilers is distilled. The residual product is then rushed over, and then fractionated on a 12 plate Vigreauz column at 88° C and 3.9–4.1 mm Hg pressure to yield the n-hexyl-2-methyl pentenoate mixture:
  n-hexyl-2-methyl-cis-3-pentenoate; and
  n-hexyl-2-methyl-4-pentenoate.

EXAMPLE L

STRAWBERRY FLAVOR

The following basic strawberry flavor is prepared:

| Ingredients | Parts by Weight |
|---|---|
| p-Hydroxybenzylacetone | 2 |
| Vanillin | 15 |
| Maltol | 20 |
| Ethyl methylphenyl glycidate | 15 |
| Benzyl acetate | 20 |
| Ethyl butyrate | 10 |
| Methyl cinnamate | 5 |
| Methyl anthranilate | 5 |
| Alpha-ionone | 1 |
| Gamma-undecalactone | 2 |
| Diacetyl | 2 |
| Anethole | 1 |
| Cis-3-hexenol | 17 |
| Ethanol (95% aqueous) | 385 |
| Propylene glycol | 500 |

To one-third of this flavor, a mixture containing a major proportion of ethyl-2-methyl-cis-3-pentenoate (prepared according to Example XLI; bulked fractions 12-31) is added at the rate of 1%. To another third of this flavor substantially pure ethyl-2-methyl-cis-3-pentenoate prepared according to Example XLII (5½ hour reaction time; distillation fraction number 22) is added at the rate of 8%. The third portion of this flavor is kept "as is". The three flavors thus produced are compared at the rate of 0.005% (50 ppm) in water by a bench panel.

The flavor containing the mixture rich in ethyl-2-methyl-cis-3-pentenoate is found to have a more fresh natural strawberry-like aroma and taste than the basic flavor formulation and is preferred over the basic formulation. The flavor containing the substantially pure ethyl-2-methyl-cis-3-pentenoate was found also to have a more natural strawberry-like aroma and taste; especially a preferred, sweet, fresh, strawberry-like aroma, and is also preferred over the basic flavor formulation.

EXAMPLE LI

The following concentrate is prepared:

| Ingredient | Percent |
| --- | --- |
| Geraniol | 1.00 |
| Ethyl methyl phenyl glycidate | 3.50 |
| Mixture containing major proportion of isobutyl-2-methyl-cis-3-pentenoate (prepared according to the process of Example XLVII) | 5.00 |
| Vanillin | 5.50 |
| Ethyl pelargonate | 13.00 |
| Isoamyl acetate | 14.00 |
| Ethyl butyrate | 58.00 |
| | 100.0 |

EXAMPLE LII

Another concentrate (3) is prepared as follows:

| Ingredient | Percent |
| --- | --- |
| Naphthyl ethyl ether | 1.0 |
| Vanillin | 2.5 |
| Ethyl methyl phenyl glycidate | 3.0 |
| Mixture containing major proportion of isobutyl-2-methyl-cis-3-pentenoate (prepared according to the process of Example XLVII) | 5.0 |
| Ethyl acetate | 9.5 |
| Isoamyl acetate | 12.0 |
| Ethyl butyrate | 26.0 |
| Isoamyl butyrate | 41.0 |
| | 100.0 |

EXAMPLE LIII

The concentrate prepared in Example LI is dissolved in 4 volumes of propylene glycol and the mixture is added to a hard candy melt at the rate of 1.5 oz. of the concentrate solution per 100 lbs. of melt. After the finished candy has been produced, it is found to have an excellent strawberry flavor. When the candy is compared with candy made under the same conditions, but without the mixture containing a major proportion of isobutyl-2-methyl-cis-3-pentenoate mixture prepared according to the process of Example XLVII in the concentrate, it is found to have an inferior strawberry flavor.

EXAMPLE LIV

The propylene glycol solution of the concentrate as prepared in Example LIII is added to a simple syrup at the rate of ⅛ oz. per gallon of syrup. The syrup is acidified by the addition of 1.5 oz. of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor and is found to be markedly superior to a beverage prepared in the same manner but without the mixture containing a major proportion of isobutyl-2-methyl-cis-3-pentenoate prepared according to the process of Example XLVII.

EXAMPLE LV

The flavor concentrate prepared in Example LI is admixed with gum arabic and in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the mixture containing a major proportion of isobutyl-2-methyl-cis-3-pentenoate mixture prepared according to the process of Example XLVII in the concentrate.

EXAMPLE LVI

FLAVOR FORMULATION MIXTURE CONTAINING MAJOR PROPORTION OF ETHYL-2-METHYL-CIS-3-PENTENOATE

The following basic strawberry formulation is prepared:

| Ingredient | Parts by Weight |
| --- | --- |
| Parahydroxy benzyl acetone | 0.2 |
| Vanillin | 1.5 |
| Maltol | 2.0 |
| Ethyl-3-methyl-3-phenyl glycidate | 1.5 |
| Benzyl acetate | 2.0 |
| Ethyl butyrate | 1.0 |
| Methyl cinnamate | 0.5 |
| Methyl anthranilate | 0.5 |
| Alpha-ionone | 0.1 |
| Gamma undecalactone | 0.2 |
| Diacetyl | 0.2 |
| Anethole | 0.1 |
| Cis-3-hexenol | 1.7 |
| 95% Aqueous ethanol | 38.5 |
| Propylene glycol | 50.0 |
| | 100.0 |

To a portion of the foregoing formulation, 0.2% by weight of "high cis" ethyl-2-methyl-3-pentenoate isomer mixture prepared according to the process of Example XL is added. The formulation containing the ethyl-2-methyl-cis-3-pentenoate is compared to the same formulation without said ethyl-2-methyl-cis-3-pentenoate.

Both flavors and evaluated in a milk beverage sweetened with 10% sugar at the rate of 100 ppm. Both beverages are tested by an expert panel. The beverage containing the strawberry formulation with the addition of ethyl-2-methyl-cis-3-pentenoate is unanimously preferred as having a more natural like, delicate strawberry aroma, a sweeter, more pleasant, strawberry taste and a sweet, strawberry after-taste.

EXAMPLE LVII

RASPBERRY PERFUME FORMULATION

The following formulation is prepared:

| Ingredient | Parts by Weight |
| --- | --- |
| Mixture containing major proportion | 10 |

-continued

| Ingredient | Parts by Weight |
|---|---|
| of ethyl-2-methyl-cis-3-pentenoate prepared according to the process of Example XL | |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl acetate | 50 |
| 4-(parahydroxyphenyl)-2-butanone | 50 |
| Ethyl laurate | 30 |
| Ethyl isovalerate | 10 |
| Ethyl Butyrate | 50 |
| Cinnamyl cinnamate | 20 |
| | 419 |

The ethyl-2-methyl-cis-3-pentenoate imparts to this raspberry perfume formulation a delicate raspberry topnote nuance.

EXAMPLE LVIII

TOBACCO FLAVOR FORMULATION AND TOBACCO

A tobacco mixture is produced by admixing the following materials:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. Half of the cigarettes are then treated with 100 or 200 ppm of the substantially pure ethyl-2-methyl-cis-3-pentenoate produced according to the process of Example XLII (5½ hour reaction time; distillation fraction number 22). The control cigarettes not containing the ethyl-2-methyl-cis-3-pentenoate produced according to the process of Example XLII and the experimental cigarettes which do contain the ethyl-2-methyl-cis-3-pentenoate produced according to the process of Example XLII are evaluated by paired comparison, and the results are as follows:

In aroma, the cigarettes containing the ethyl-2-methyl-cis-3-pentenoate have been found to be more aromatic.

In smoke flavor, the cigarettes containing the ethyl-2-methyl-cis-3-pentenoate are more aromatic, more sweet, more bitter, slightly less harsh in the mouth and throat and leave a slight, sweet chemical mouth-coating effect similar to Turkish tobacco.

In summary, the ethyl-2-methyl-cis-3-pentenoate enhances the tobacco-like taste and aroma of a blended cigarette and imparts to that cigarette a Turkish-like character in smoke flavor.

EXAMPLE LIX

The following concentrate is prepared:

| Ingredient | Percent |
|---|---|
| Geraniol | 1.00 |
| Ethyl methyl phenyl glycidate | 3.33 |
| Substantially pure ethyl-2-methyl-cis-3-pentenoate prepared according to the process of Example XLII (5 ½ hour reaction time; distillation fraction number 22) | 4.77 |
| Vanillin | 5.66 |
| Ethyl pelargonate | 13.06 |
| Isoamyl acetate | 14.00 |
| Ethyl butyrate | 58.18 |

EXAMPLE LX

| Ingredient | Percent |
|---|---|
| Naphthyl ethyl ether | 0.96 |
| Vanillin | 2.66 |
| Ethyl methyl phenyl glycidate | 2.88 |
| Substantially pure ethyl-2-methyl-cis-3-pentenoate prepared according to the process of Example XLII (5 ½ hour reaction time; distillation fraction number 22) | 4.90 |
| Ethyl acetate | 9.58 |
| Isoamyl acetate | 12.25 |
| Ethyl butyrate | 26.20 |
| Isoamyl butyrate | 40.57 |

EXAMPLE LXI

100 Parts of the concentrate prepared in Example LIX is dissolved in 400 parts of propylene glycol and the mixture is added to a hard candy melt at the rate of 1.5 oz of the concentrate solution per 100 lbs. of melt. After the finished candy has been produced, it is found to have an excellent strawberry flavor. When the candy is compared with candy made under the same conditions, but without the ethyl-2-methyl-cis-3-pentenoate prepared according to the process of Example XLII in the concentrate, it is found to have an inferior strawberry flavor.

EXAMPLE LXII

A propylene glycol solution of the concentrate (1 part concentrate: 4parts of propylene glycol) as prepared in Example LX is added to a simple syrup at the rate of ⅛ oz. per gallon of syrup. The syrup is acidified by the addition of 1.5 oz of 50% aqueous citric acid solution to each gallon of syrup. A carbonated beverage is prepared by admixing one oz. of the flavored, acidified syrup with 5 oz. of carbonated water. The beverage so prepared has an excellent fresh strawberry flavor, and is found to be markedly superior to a beverage prepared in the same manner but without the ethyl- 2-methyl-cis-3-pentenoate prepared according to the process of Example XLII.

EXAMPLE LXIII

The flavor concentrate prepared in Example LX is admixed with gum arabic in the proportion of 7 lbs. of concentrate to 28 lbs. of gum arabic in 65 lbs. of water, and the aqueous mixture is spray-dried. The flavor concentrate-carrier combination so obtained is then added to a gelatin dessert mix in the ratio of 1 oz. of spray-dried material to 100 lbs. of dessert mix powder. The gelatin dessert produced from the mix has an excellent strawberry flavor and is markedly superior to a gelatin dessert prepared in the same manner without the ethyl-2-methyl-cis-3-pentenoate prepared according to the process of Example XLII in the concentrate.

EXAMPLE LXIV

RASPBERRY PERFUME FORMULATION

The following formulation is prepared:

| Ingredient | Parts by Weight |
| --- | --- |
| Substantially pure ethyl-2-methyl-cis-3-pentenoate prepared according to the process of Example LXII (5 ½ hour reaction time; distillation fraction number 22) | 10 |
| Ethyl-3-methyl-3-phenyl glycidate | 150 |
| Vanillin | 5 |
| 3-Hydroxy-2-methyl-4-pyrone | 10 |
| Beta-ionone | 30 |
| Ethyl acetate | 1 |
| Ethyl acetoacetate | 2 |
| Diacetyl | 1 |
| Heliotropyl Acetate | 50 |
| 4-(parahydroxyphenyl)-2-butanone | 50 |
| Ethyl laurate | 30 |
| Ethyl isovalerate | 10 |
| Ethyl butyrate | 50 |
| Cinnamyl cinnamate | 20 |
| | 419 |

The ethyl-2-methyl-cis-3-pentenoate imparts to this raspberry perfume formulation a delicate raspberry topnote nuance.

| Ingredient | Parts by Weight |
| --- | --- |
| Cab-O-Sil®M-5 (Brand of Silica produced by the Cabot Corporation of 125 High Street, Boston, Mass. 02110; Physical Properties: Surface Area: 200 m²/gm Nominal Particle Size: 0.012 microns Density: ⅖ lbs/cu.ft. | 3.2 |

The Cab-O-Sil is dispersed in any of the exemplified liquid flavor compositions with vigorous stirring, thereby resulting in a viscous liquid. 48.4 Parts by weight of the powder flavor composition prepared in Part A is then blended into the said viscous liquid, with stirring at 25° C for a period of 30 minutes, resulting in a thixotropic sustained release flavor paste.

EXAMPLE LXVI

CHEWING GUM

100 Parts by weight of chicle are mixed with 4 parts by weight of the flavor prepared in accordance with Example LXV. 300 Parts of sucrose and 100 parts of corn syrup are added. Mixing is effected in a ribbon blender with jacketed side walls of the type manufactured by the Baker Perkins Co.

The resultant chewing gum blend in then manufactured into strips 1 inch in width and 0.1 inches in thickness. The strips are cut into lengths of 3 inches each. On chewing the chewing gum has a pleasant long lasting strawberry flavor.

EXAMPLE LXVII

TOOTHPASTE FORMULATION

The following separate groups of ingredients are prepared:

| Group "A" | |
| --- | --- |
| 30.200 | Glycerin |
| 15.325 | Distilled water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example LXXIX |
| 100.00 (Total) | |

PROCEDURE:

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant strawberry flavor, of constant strong intensity throughout said procedure (1–1.5 minutes).

EXAMPLE LXVIII

CHEWABLE VITAMIN TABLETS

The flavor material produced according to the process of Example LXV is added to a Chewable Vitamin Tablet Formulation at a rate of 5 gm/gm which Chewable Vitamin Tablet Formulation is prepared as follows:

| | Gms/1000 tablets |
| --- | --- |
| Vitamin C (ascorbic acid) as ascorbic acid-sodium ascorbate mixture 1:1 | 70.0 |
| Vitamin B₁ (thiamine mononitrate) as Rocoat thiamine mononitrate 33⅓% (Hoffman La Roche) | 4.0 |
| Vitamin B₂ (riboflavin) as Rocoat riboflavin 33⁻% | 5.0 |

|  | Gms/1000 tablets |
| --- | --- |
| Vitamin B<sub>6</sub> (pyridoxine hydrochloride) as Rocoat pyridoxine hydrochloride 33⅓% | 4.0 |
| Niacinamide as Rocoat niacinamide 33⅓% | 33.0 |
| Calcium pantothenate | 11.5 |
| Vitamin B<sub>12</sub> (cyanocobalamin) as Merk 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example LXXIX | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablet yields a pleasant, long-lasting, consistently strong strawberry flavor for a period of 12 minutes.

What is claimed is:

1. A process for augmenting or enhancing the berry fruit flavor of a foodstuff which comprises adding thereto, as the sole ingredient for augmenting or enhancing berry fruit flavor, and in an amount of from 0.10 ppm up to 50 ppm, based on the total weight of said foodstuff, a composition consisting essentially of one or more synthetically-produced 6-carbon carboxylic acid ester-containing composition, each of which comprises as its major constituent, a cis ester of 2-methyl-3-pentenoic acid having the structure:

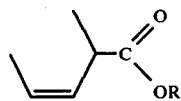

wherein R is selected from the group consisting of ethyl, isobutyl and n-hexyl.

2. The process of claim 1 wherein the 6-carbon carboxylic acid ester-containing composition consists essentially of an approximately 3:2 cis:trans isomer mixture of an alkyl ester of 2-methyl-3-pentenoic acid having the structure:

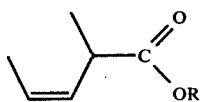

wherein R is ethyl, isobutyl or n-hexyl

3. The process of claim 1 wherein the 6-carbon carboxylic acid ester-containing composition consists essentially of a mixture consisting of 80% alkyl ester of 2-methyl-cis-3-pentenoic acid having the structure:

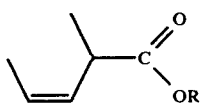

wherein R is selected from the group consisting of ethyl, isobutyl and n-hexyl and 20% of a corresponding alkyl ester of 2-methyl-2-pentenoic acid.

4. The process of claim 1 wherein the 6-carbon carboxylic acid ester-containing composition consists essentially of at least two 6-carbon atom-containing carboxylic acid ethyl, isobutyl or n-hexyl esters with the alkoxy moieties being the same in each of the esters present in the composition, and contains:

a. more than 60% by weight of at least one 2-methyl-cis-3-pentenoic acid ethyl, isobutyl or n-hexyl ester; and b. less than 40% by weight of at least one compound selected from the group consisting of:
   i. at least one 2-methyl-4-pentenoic acid ethyl, isobutyl or n-hexyl ester; and
   ii. at least one 2-methyl-pentanoic acid ethy, isobutyl or n-hexyl ester.

5. A flavor modifying composition useful in augmenting or enhancing the berry fruit flavor of a foodstuff consisting essentially of (i) from about 0.05% up to about 10% by weight based on the total weight of said flavoring composition of one or more synthetically produced 6-carbon carboxylic acid estercontaining compositions comprising as their major constituent, at last one alkyl ester of 2-methyl-cis-pentenoic acid having the structure:

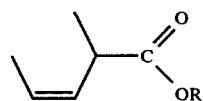

wherein R is selected from the group consisting of ethyl, isobutyl and n-hexyl and (ii) the remainder of said composition being at least one flavor adjuvant, selected from the group consisting of para-hydroxy benzyl acetone, vanillin, maltol, ethyl-3-methyl-3-phenyl glycidate, benzyl acetate, ethyl butyrate, methyl cinnamate, methyl anthranilate, alpha-ionone, gamma undecalactone, diacetyl, anethole, cis-3-hexenol, 2-(4-hydroxy-4-methylpentyl) norbornadiene, beta ionone, isobutyl acetate, dimethyl sulfide, acetic acid, acetaldehyde, 4-(2,6,6-trimethyl-1,3-cyclohexadiene-1-yl)-2butanone, 4-(6,6-dimethyl-2-methylene-3-cyclohexen-1-yl)-2-butanone, geraniol, ethyl pelargonate, isoamyl acetate, naphthyl ethyl ether, ethyl acetate, isoamyl butyrate, 2-methyl-2-pentenoic acid, 2-methyl-3-pentenoic acid, 4-allyl-1,2,6-trimethoxy benzene and 4-(1-propenyl)-1,2,6-trimethoxy benzene.

6. The flavor modifying composition of claim 5 wherein the 6-carbon carboxylic acid ester-containing composition consists essentially of an approximately 3:2 cis:trans isomer mixture of at least one alkyl ester of 2-methyl-3-pentenoic acid having the structure:

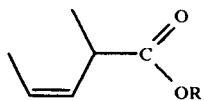

wherein R is selected from the group consisting of ethyl, isobutyl and n-hexyl.

7. The flavor modifying composition of claim 5 wherein the 6-carbon carboxylic acid ester composition consists essentially of a mixture consisting of 80% of an alkyl ester of 2-methyl-cis-3-pentenoic acid having the structure:

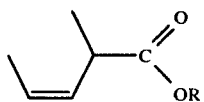

wherein R is selected from the group consisting of ethyl, isobutyl and n-hexyl and 20% of a corresponding alkyl ester of 2-methyl-2-pentenoic acid 8. The flavor modifying composition of claim 5 wherein the 6-carbon carboxylic acid ester composition consists essentially of at least two 6-carbon atom-containing carboxylic acid ethyl, isobutyl or n-hexyl esters and contains:
 a. more than 60% by weight of at least one 2-methyl-cis-3-pentenoic acid ethyl, isobutyl or n-hexyl ester; and dd
 b. less than 40% by weight of at least one corresponding ethyl, isobutyl or n-hexyl ester selected from the group consisting of:
  i. at least one corresponding 2-methyl-4-pentenoic acid ethyl, isobutyl of n-hexyl ester; and
  ii. at least one corresponding 2-methyl-pentatoic acid ethyl, isobutyl or n-hexyl ester.

* * * * *